US007211064B2

(12) United States Patent
Shue et al.

(10) Patent No.: US 7,211,064 B2
(45) Date of Patent: May 1, 2007

(54) DISPOSABLE SYRINGE

(76) Inventors: Ming-Jeng Shue, No. 14, Lane 8, Chung-I St., Hsi Dist, Taichung City (TW); Deborah Huang, 7F, No. 5, Sec. 3, Liu-Chun E. Rd., Chung Dist., Taichung City (TW); Phillip Shue, No. 14, Lane 8, Chung-I St., Hsi Dist, Taichung City (TW)

( * ) Notice: Subject to any disclaimer, the term of this patent is extended or adjusted under 35 U.S.C. 154(b) by 630 days.

(21) Appl. No.: 10/667,588

(22) Filed: Sep. 22, 2003

(65) Prior Publication Data

US 2004/0215150 A1 Oct. 28, 2004

(30) Foreign Application Priority Data

Apr. 22, 2003 (TW) ............................... 92109392 A

(51) Int. Cl.
*A61M 5/00* (2006.01)
(52) U.S. Cl. ...................................... 604/110; 604/187
(58) Field of Classification Search ................ 604/110, 604/263, 187, 192–198, 181; 128/919
See application file for complete search history.

(56) References Cited

U.S. PATENT DOCUMENTS

| 4,840,185 A | 6/1989 | Hernandez |
| 4,874,382 A | 10/1989 | Haughton |
| 4,955,870 A | 9/1990 | Sudharto |
| RE33,585 E | 5/1991 | Haber et al. |
| 5,084,029 A | 1/1992 | Nacci |
| 5,088,988 A | 2/1992 | Talonn et al. |
| 5,114,404 A * | 5/1992 | Paxton et al. ................ 604/110 |
| 5,129,884 A | 7/1992 | Dysarz |
| 5,211,628 A * | 5/1993 | Marshall ...................... 604/110 |
| 5,389,076 A | 2/1995 | Shaw |
| 6,436,075 B1 | 8/2002 | Liao |

FOREIGN PATENT DOCUMENTS

| WO | WO 96 27403 | 9/1996 |
| WO | WO 98 48869 | 11/1998 |
| WO | WO 00 18454 | 4/2000 |

* cited by examiner

*Primary Examiner*—Matthew F. DeSanto
(74) *Attorney, Agent, or Firm*—Woodard, Emhardt, Moriarty, McNett & Henry LLP

(57) ABSTRACT

A disposable syringe includes a plunger movable in a barrel relative to a needle seat that engages an inner surrounding barrel wall surface of the barrel by a resisting force. The plunger includes a plunger body and a coupling rod which is in frictional engagement with the plunger body and which has a central anchored area disposed to engage an anchoring portion of the needle seat by a holding force. As such, when the plunger body is moved to bring the central anchored area into engagement with the anchoring portion, the resisting force is overcome to permit disengagement of the needle seat from the barrel, and the coupling rod and the needle seat can be retracted into the plunger body by virtue of a biasing action of a biasing member.

14 Claims, 27 Drawing Sheets

DISPOSABLE SYRINGE

CROSS-REFERENCE TO RELATED APPLICATION

This application claims priority of Taiwanese application No. 092109392, filed on Apr. 22, 2003.

BACKGROUND OF THE INVENTION

1. Field of the Invention

This invention relates to a disposable syringe, more particularly to a disposable syringe which enables a needle cannula to be retracted into a plunger body.

2. Description of the Related Art

Referring to FIGS. 1 and 2, U.S. Pat. No. 5,211,628 discloses a syringe with an automatic retracting needle, which includes a barrel 11 with a chamber, a flexible lock member 12 fixed in the chamber adjacent to a lower end 111 thereof, a flexible needle seat 13 positioned in the chamber adjacent to the lower end 111 and formed with an opening 131, a needle cannula 14 fastened to the needle seat 13 in the opening 131 and extending through an orifice 112 in the lower end 111, a plunger 15 slidable in the chamber along an axis (X), a shaft 16 disposed in the plunger 15 and having an integral annular lower foot part 161 which is press-fitted against an upwardly extending lip 151 of the plunger 15, and a spring 17 surrounding the shaft 16 and having one end 172 which abuts against an upper end 163 of the shaft 16 and the other end 171 which is retained in a compressed state by engagement of the lip 151 with the lower foot part 161. The lock member 12 has a flexible inwardly protruding lip 121 which bears on a shoulder 134 of the needle seat 13 to prevent the needle seat 13 from moving upwardly.

The shaft 16 further includes a lower protrusion 162 shaped to mate with the opening 131. As such, when the plunger 15 is pressed downwardly along the axis (X), the lower protrusion 162 can be inserted into the opening 131, and the lower foot part 161 spreads the lip 121 outwardly so that the lip 121 is bent to disengage from the shoulder 134. At the same time, the residual force of the lip 121 against the lower foot part 161 causes a slight inward bend of the lower foot part 161 and momentarily causes the lower foot part 161 to lose contact with the lip 151. The compressive force of the spring 17 then urges the upper end 163 of the shaft 16 upwardly. Due to the mating fit of the lower protrusion 162 with the opening 131, the upward movement is also transferred to the needle seat 13 and the needle cannula 14 which are urged upwardly into the plunger 15.

However, in order to ensure smooth retraction of the needle seat 13 and the needle cannula 14 into the plunger 15, the engagement of the lower foot part 161 with the lip 151 cannot be very tight. However, a loose engagement may result in an undesired release of the compressive force of the spring 17. Moreover, some medicine may enter the plunger 15 from a clearance between the lower foot part 161 and the lip 151. Furthermore, the lower foot part 161, which has a conical shape, may interfere with the retraction of the shaft 16 into the plunger 15.

SUMMARY OF THE INVENTION

The object of the present invention is to provide a disposable syringe which can be operated easily and smoothly to retract a used needle into a plunger body.

According to this invention, the disposable syringe includes a barrel which has an inner surrounding barrel wall surface surrounding an axis and confining a passage. The passage has open lower and upper ends opposite to each other in a longitudinal direction parallel to the axis. The inner surrounding barrel wall surface includes a larger-diameter segment and a smaller-diameter segment which are disposed proximate to the open lower and upper ends, respectively, to form a surrounding shoulder portion therebetween. The smaller-diameter segment includes a front surrounding region and a rear surrounding region which is proximate to the surrounding shoulder portion. The larger-diameter segment includes proximate and distal surrounding regions respectively disposed proximate to and distal from the surrounding shoulder portion.

A tubular needle seat includes a hub portion which is disposed to fix a needle cannula therein, and which has a surrounding front end wall extending radially relative to the axis, a surrounding gripped portion extending from the hub portion, and an anchoring portion extending from the surrounding gripped portion.

A grip member is disposed to bring the surrounding gripped portion into engagement with one of the rear surrounding region and the proximate surrounding region. The grip member can provide a resisting force that holds the surrounding gripped portion in position so as to prevent movement of the surrounding gripped portion relative to a respective one of the rear surrounding region and the proximate surrounding region during a piercing action of the needle cannula for a hypodermic injection, and that permits disengagement of the surrounding gripped portion from the respective one of the rear surrounding region and the proximate surrounding region so as to enable a subsequent movement of the tubular needle seat relative to the inner surrounding barrel wall surface when the surrounding gripped portion is subjected to a first external force.

A plunger, in a position of use, is disposed to be movable in the larger-diameter segment, and includes a plunger body and a coupling rod.

The plunger body includes a top end wall movable towards the anchoring portion, a bottom end wall opposite to the top end wall, and a tubular intermediate wall interposed between the top and bottom end walls and confining an accommodation chamber. The top end wall has an inner peripheral edge portion defining an access opening therein, which is communicated with the accommodation chamber.

The coupling rod includes an upper coupling end which is inserted in the access opening, and which has a central anchored area that is engageable with the anchoring portion by a holding force such that engagement of the central anchored area with the anchoring portion is not disrupted during the disengagement of the surrounding gripped portion from the respective one of the rear surrounding region and the proximate surrounding region. The upper coupling end further has a surrounding abutment area which surrounds the central anchored area, and which is in frictional engagement with the inner peripheral edge portion. As such, when the upper coupling end is depressed towards the bottom end wall by virtue of movement of the tubular needle seat relative to the upper coupling end, the coupling rod is disengaged from the inner peripheral edge portion so as to enable the coupling rod to be forced from the position of use to a retracted position where the coupling rod is disposed closer to the bottom end wall. The coupling rod further includes a shank portion extending from the upper coupling end towards the bottom end wall and terminating at a thrust end.

A biasing member is disposed between the shank portion and the tubular intermediate wall to bias the coupling rod towards the retracted position.

A retaining member is disposed to retain the thrust end in the position of use against biasing action of the biasing member.

A triggering member is disposed to prevent the retaining member from retaining the thrust end in response to a second external force, thereby permitting the coupling rod to be biased towards the retracted position.

BRIEF DESCRIPTION OF THE DRAWINGS

Other features and advantages of the present invention will become apparent in the following detailed description of the preferred embodiments of the invention, with reference to the accompanying drawings, in which.

DETAILED DESCRIPTION OF THE PREFERRED EMBODIMENTS

Figure 1:
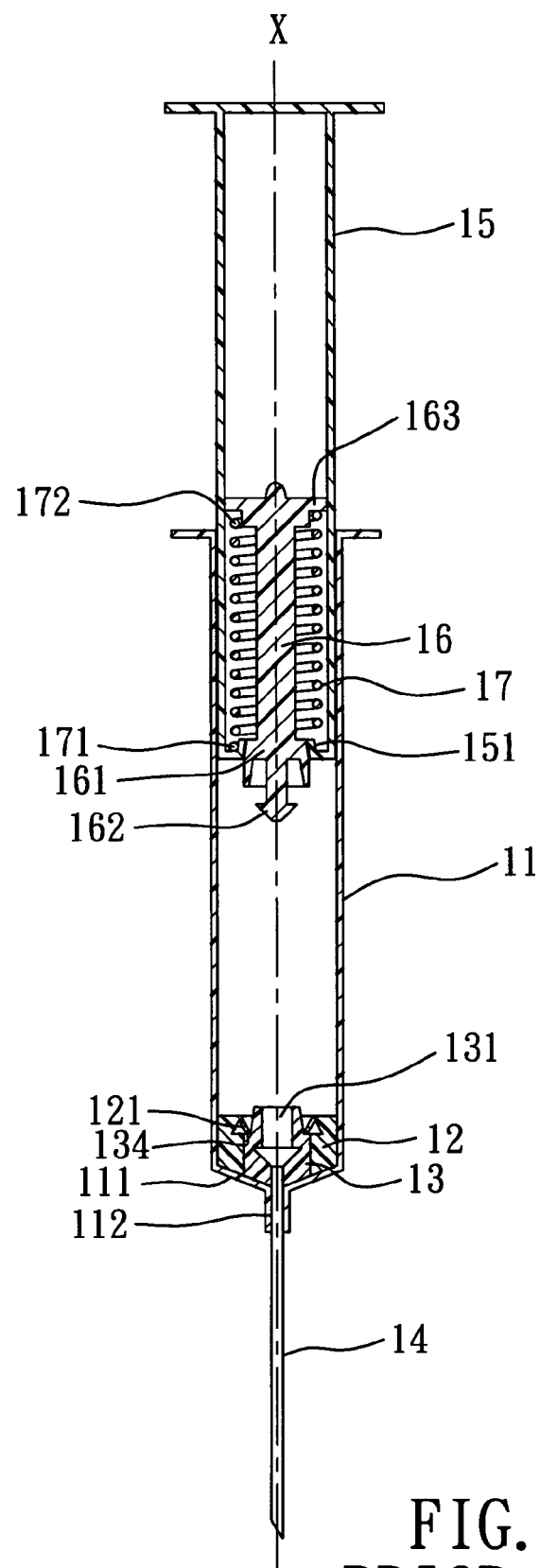
FIG. 1 is a sectional view of a conventional syringe.
Figure 2:
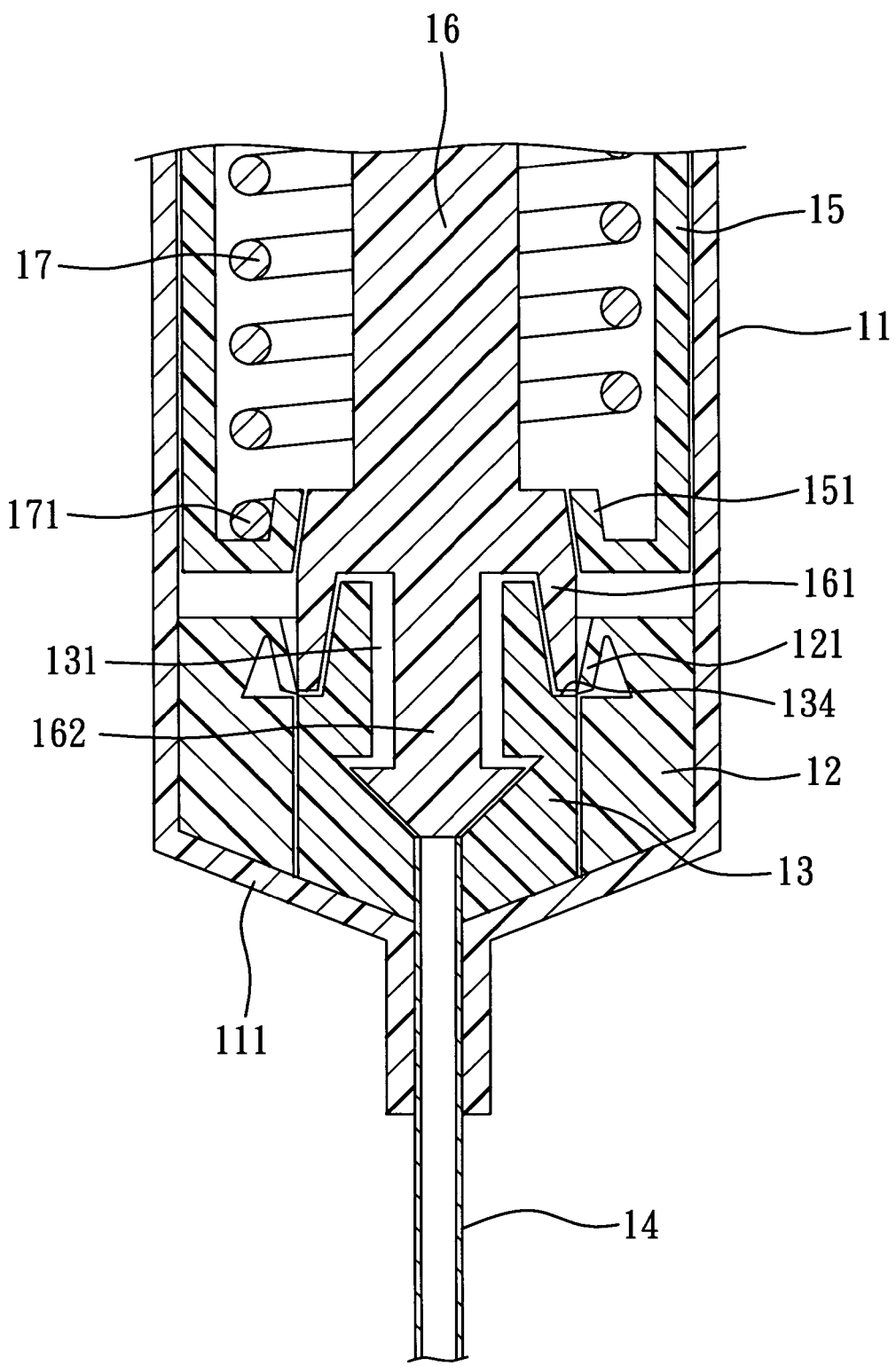
FIG. 2 is a fragmentary sectional view of the conventional syringe after use.

Before the present invention is described in greater detail, it should be noted that same reference numerals have been used to denote like elements throughout the specification.

Figure 3:
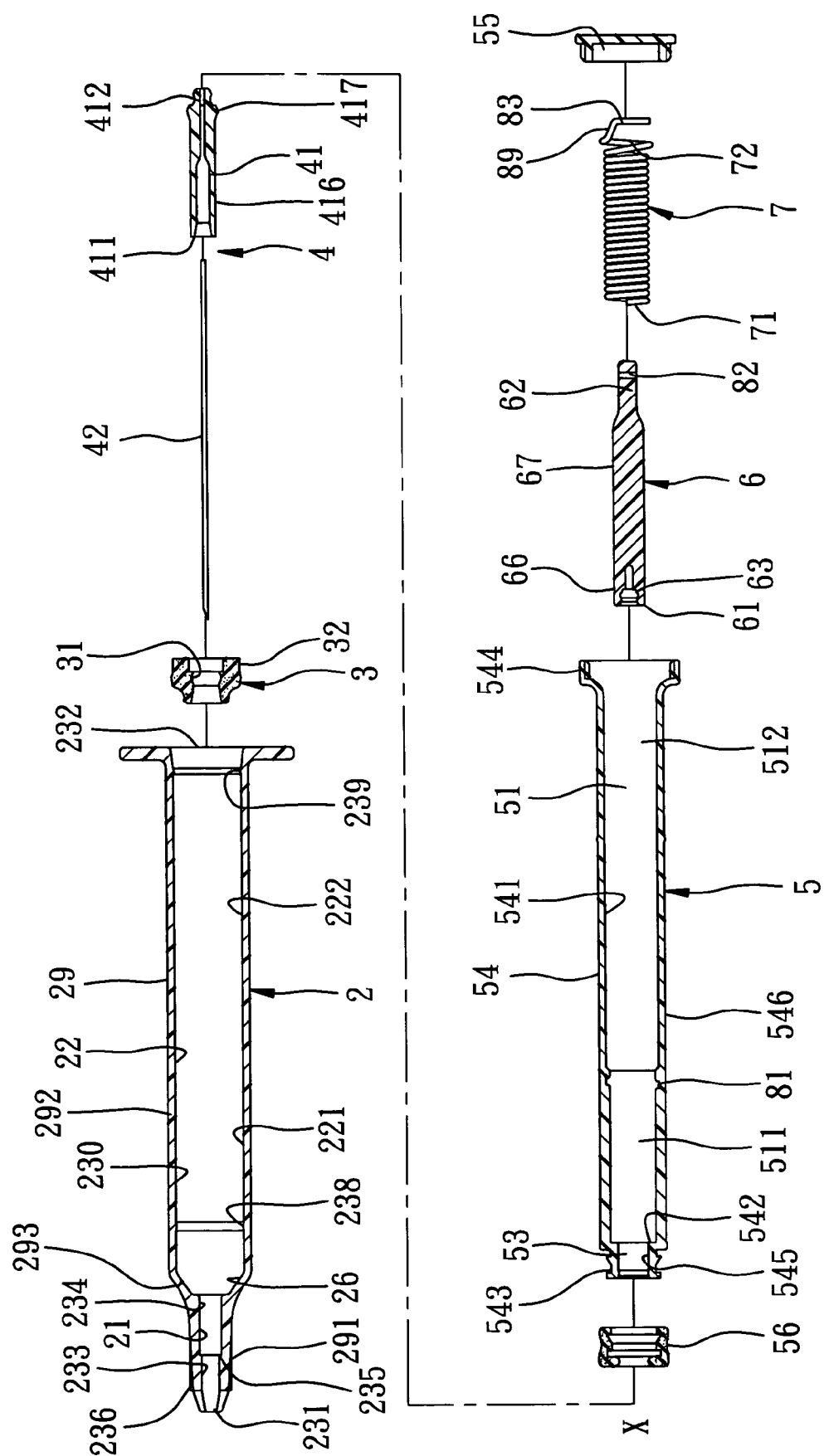
FIG. 3 is an exploded sectional view of the first preferred embodiment of a disposable syringe according to this invention.
Figure 4:
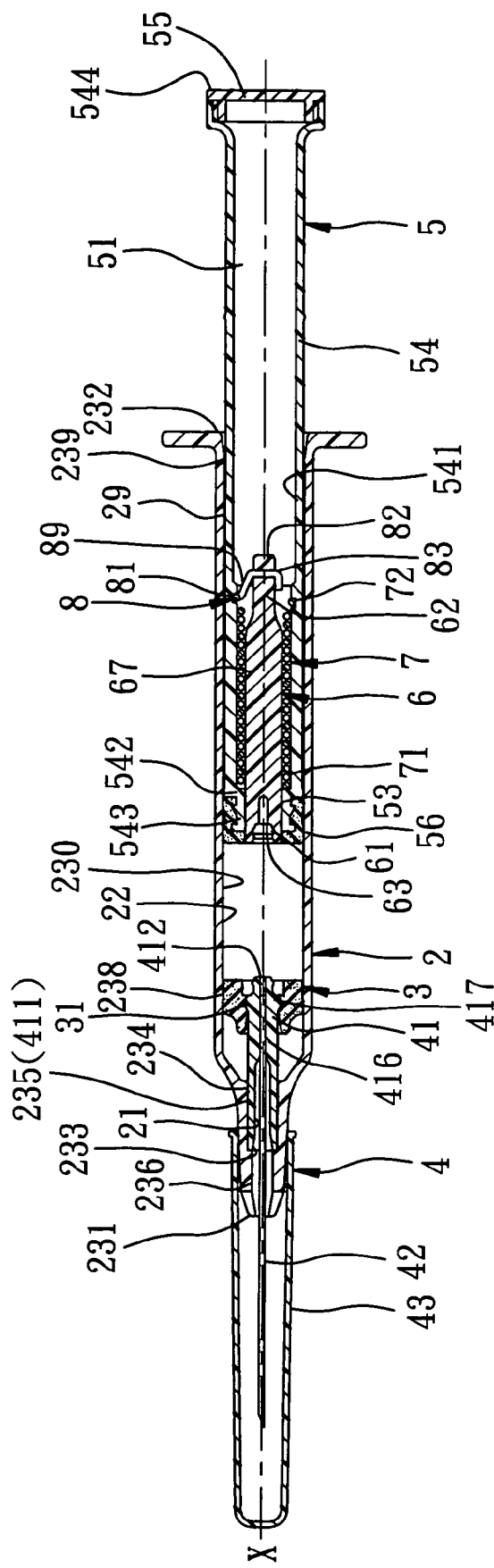
FIG. 4 is a sectional view of the first preferred embodiment in a state of use.

Referring to FIGS. 3 and 4, the first preferred embodiment of a disposable syringe according to the present invention is shown to comprise a barrel 2, a needle assembly 4 including a needle cannula 42, a tubular needle seat 41 and a tip protector 43, a grip member 3, a plunger, a biasing member 7, a retaining member 8 and a triggering member.

The barrel 2 has an inner surrounding barrel wall surface 230 which surrounds an axis (X) and which confines a passage. The passage has an open lower end 232 and an open upper end 231 which are disposed opposite to each other in a longitudinal direction parallel to the axis (X). The inner surrounding barrel wall surface 230 includes a larger-diameter segment 22 and a smaller-diameter segment 21 which confine rear and front passageways, respectively, and which are disposed proximate to the open lower end 232 and the open upper end 231, respectively, to form a surrounding shoulder portion 26 therebetween. The smaller-diameter segment 21 includes a front surrounding region 233, a rear surrounding region 234 which is proximate to the surrounding shoulder portion 26, and a shoulder 235 which is disposed between the front and rear surrounding regions 233,234. The larger-diameter segment 22 includes proximate and distal surrounding regions 221,222 which are opposite to each other in the longitudinal direction and which are respectively proximate to and distal from the surrounding shoulder portion 26. The proximate and distal surrounding regions 221,222 are formed with retaining protrusions 238,239, respectively. The barrel 2 further has an outer surrounding barrel wall surface 29 which surrounds the axis (X), and which includes front and rear outer surrounding segments 291,292 that are disposed opposite to the smaller-diameter segment 21 and the larger-diameter segment 22 in directions radial to the axis (X), respectively, and a transition surrounding segment 293 which is interposed between the front and rear outer surrounding segments 291,292, and which diverges gradually from the front outer surrounding segment 291 to the rear outer surrounding segment 292. A rib portion 236 is disposed on the front outer surrounding segment 291, and extends in the longitudinal direction to the transition surrounding segment 293.

The needle seat 41 includes a hub portion 416 which is disposed to fix the needle cannula 42 therein, and which has a surrounding front end wall 411 extending radially relative to the axis (X), a surrounding gripped portion 417 which extends from the hub portion 416 in the longitudinal direction and away from the surrounding front end wall 411, and an anchoring portion 412 which extends from the surrounding gripped portion 417 in the longitudinal direction and away from the hub portion 416. The surrounding front end wall 411 is disposed to abut against the shoulder 235 so as to block forward movement of the needle seat 41. The needle cannula 42 extends through the open upper end 231. The tip protector 43 is sleeved frictionally on the rib portion 236 for shielding the needle cannula 42. Note that the extension of the rib portion 236 onto the transition surrounding segment 293 ensures the firm engagement between the tip protector 43 and the rib portion 236.

Figure 5:
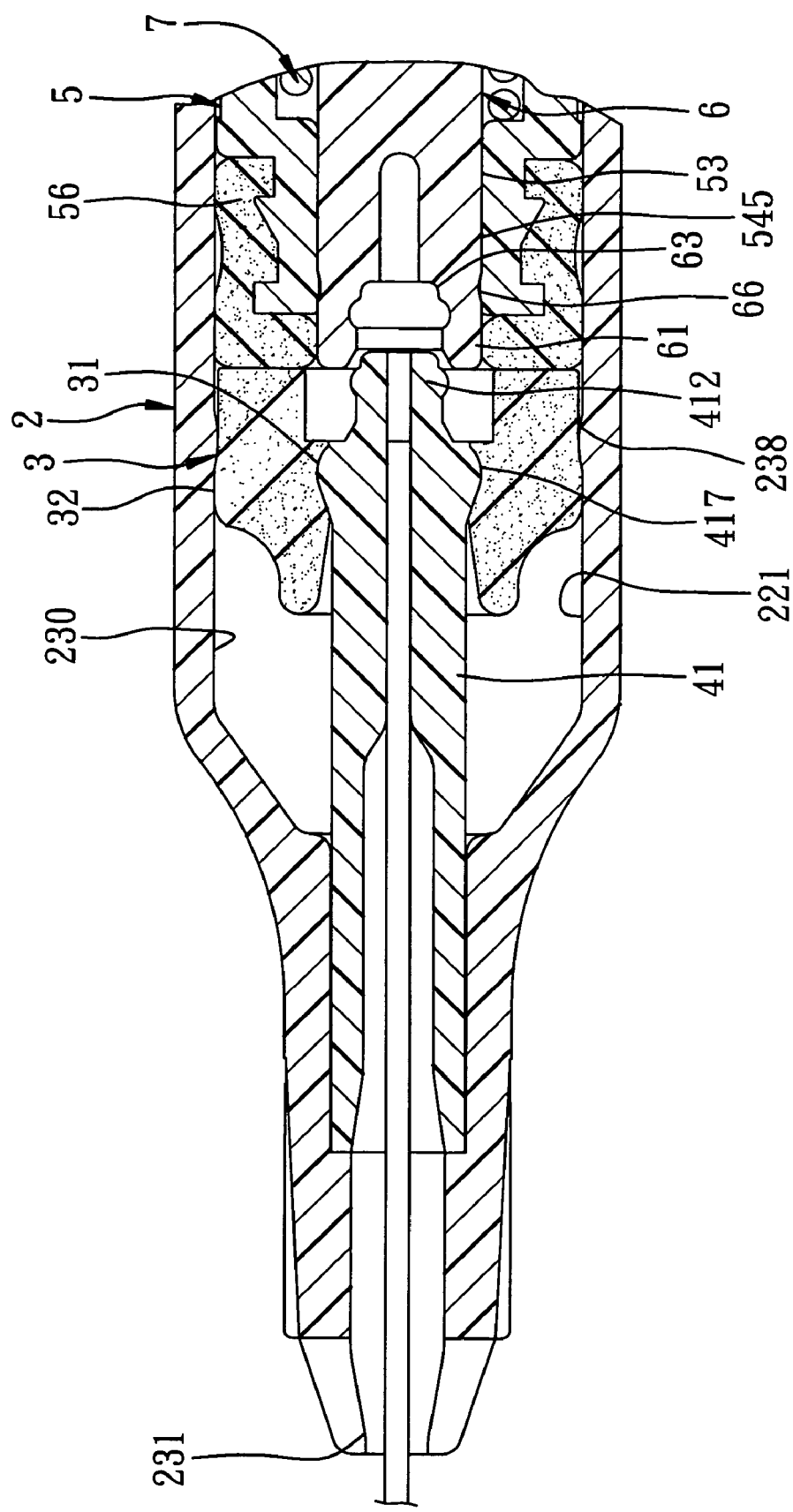
FIGS. 5 to 7 are fragmentary sectional views of the first preferred embodiment, showing a grip member in three different states.

With reference to FIG. 5, a grip member 3 includes an outer grip wall surface 32 which engages retainingly the retaining protrusion 238 with a first frictional force and which is in water-tight engagement with the proximate surrounding region 221, and an inner grip wall surface 31 which is opposite to the outer grip wall surface 32 in radial directions relative to the axis (X) and which engages retainingly the surrounding gripped portion 417 of the needle seat 41 with a second frictional force that, together with the first frictional force, provides a resisting force. Thus, the surrounding gripped portion 417 of the needle seat 41 is brought into engagement with the proximate surrounding region 221 through the grip member 3. The resisting force (i.e. the first and second frictional forces) can hold the surrounding gripped portion 417 in position so as to prevent movement of the surrounding gripped portion 417 relative to the proximate surrounding region 221 during a piercing action of the needle cannula 42 for a hypodermic injection, and can permit disengagement of the surrounding gripped portion 417 from the proximate surrounding region 221 to enable a subsequent movement of the needle seat 41 relative to the inner surrounding barrel wall surface 230 when the surrounding gripped portion 417 is subjected to a first external force.

The plunger includes a plunger body 5 and a coupling rod 6, and is disposed to be movable in the larger-diameter segment 22 in a position of use.

The plunger body 5 includes a top end wall 543 which is disposed to be movable towards the anchoring portion 412, a bottom end wall 544 which is opposite to the top end wall 543 in the longitudinal direction, and which extends outwardly of the open lower end 232 so as to be manually operable, and a tubular intermediate wall 54 which is interposed between the top and bottom end walls 543,544, and which confines an accommodation chamber 51. The accommodation chamber 51 includes front and rear chamber regions 511,512 which are respectively proximate to the top and bottom end walls 543,544, and the rear chamber region 512 has an inner diameter larger than that of the front chamber region 511. The top end wall 543 has an inner peripheral edge portion 545 which surrounds the axis (X), and which defines an access opening 53 therein to be communicated with the accommodation chamber 51. A deformable surrounding ring 56 is sleeved retainingly on the top end wall 543. The tubular intermediate wall 54 has outer and inner tubular wall surfaces 546,541 opposite to each other in radial directions relative to the axis (X). An end cap 55 is disposed to cover the bottom end wall 544.

The coupling rod 6 includes an upper coupling end 61 and a shank portion 67. The upper coupling end 61 is inserted in the access opening 53, and has a central anchored area 63 which has an engaging recess that confronts the anchoring portion 412 and that extends in the longitudinal direction so as to be engageable with the anchoring portion 412. In this embodiment, the engaging recess and the anchoring portion 412 are shaped to mate with each other with a holding force such that the engagement of the central anchored area 63 with the anchoring portion 412 is not disrupted during the disengagement of the surrounding gripped portion 417 from the proximate surrounding region 221. The upper coupling end 61 further has a surrounding abutment area 66 which surrounds the central anchored area 63, and which is disposed to be in frictional engagement with the inner peripheral edge portion 545. As such, when the upper coupling end 61 is depressed towards the bottom end wall 544 by virtue of movement of the needle seat 41 relative to the upper coupling end 61, the coupling rod 6 is disengaged from the inner peripheral edge portion 545 so as to enable the coupling rod 6 to be forced from the position of use to a retracted position where the coupling rod 6 is disposed closer to the bottom end wall 544. The shank portion 67 extends from the upper coupling end 61 towards the bottom end wall 544, and terminates at a thrust end 62.

The retaining member 8 includes a spiral retaining groove 81 which is formed in the inner tubular wall surface 541 at the front chamber region 511, which extends radially towards the outer tubular wall surface 546, and which is displaced from the top end wall 543, and a positioning groove 82 which is formed in the thrust end 62.

The biasing member 7 is a coiled spring 7 that surrounds the shank portion 67. The coiled spring 7 has an upper end 71 which abuts against a step portion 542 of the top end wall 543, and a lower end 72 opposite to the upper end 71 and having a diameter substantially larger than that of the upper end 71. The lower end 72 is inserted into and is retained in the retaining groove 81 against a biasing action of the coiled spring 7 so as to retain the thrust end 62 in the position of use against the biasing action.

In this embodiment, the triggering member includes an actuated portion which is formed integrally with the coiled spring 7. The actuated portion has a pushed end 83 which is inserted into the positioning groove 82 to be moved with the thrust end 62, and a pulling end 89 which is disposed to pull the lower end 72 out of the retaining groove 81 once the pushed end 83 is moved downwardly with the thrust end 62 when the upper coupling end 61 is depressed to be disengaged from the inner peripheral edge 545 in response to a second external force, thereby enabling the coupling rod 6 to be forced by virtue of the biasing action of the coiled spring 7 to move to the retracted position.

In use, the plunger body 5 is pressed forwardly to push the surrounding ring 56 against the grip member 3 to complete an injection course. In this state, a part of the anchoring portion 412 is inserted into the engaging recess of the central anchored area 63, as shown in FIG. 5.

Figure 6:
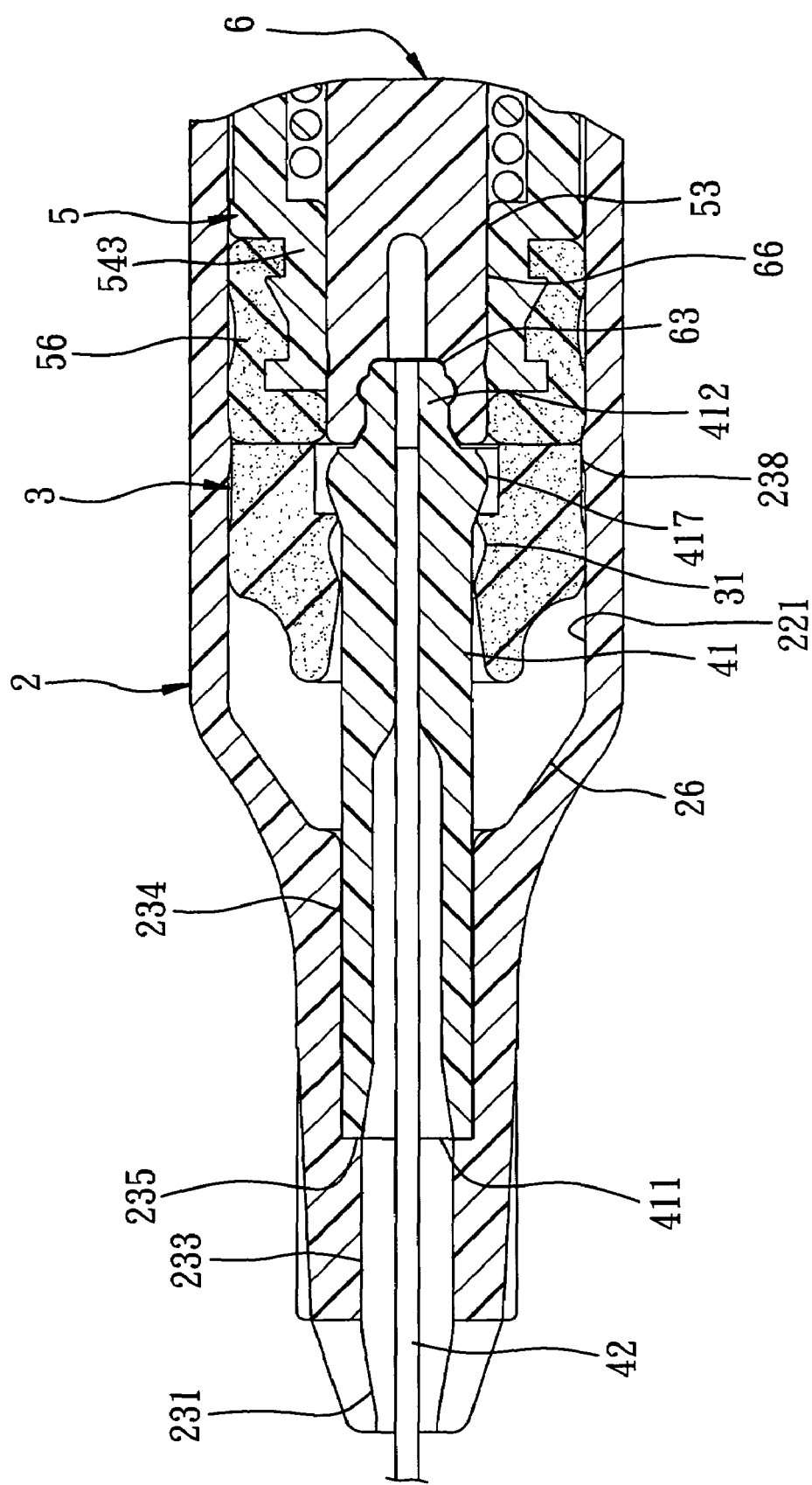

Subsequently, referring to FIG. 6, when a pushing force, i.e. the aforesaid first external force, which is greater than the resisting force, is further applied to the plunger body 5, the top end wall 543 and the surrounding ring 56 are moved to push the grip member 3 towards the surrounding shoulder portion 26 relative to the surrounding grip portion 417 due to the abutment of the surrounding front end wall 411 against the shoulder 235. The surrounding grip portion 417 is then disengaged from the inner grip wall surface 31 and from the proximate surrounding region 221, thereby enabling the anchoring portion 412 to engage the engaging recess of the central anchored area 63.

Figure 7:
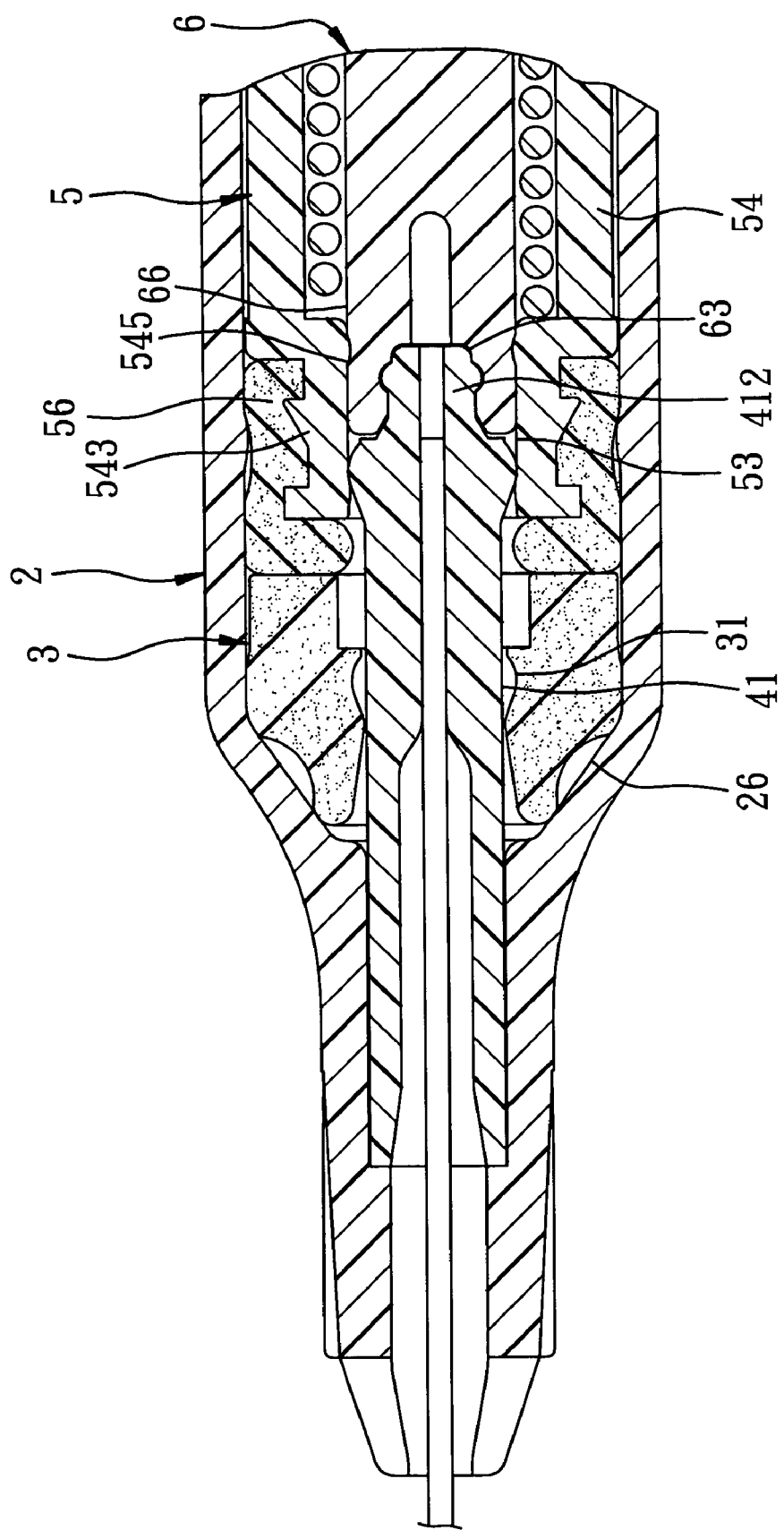
Figure 8:
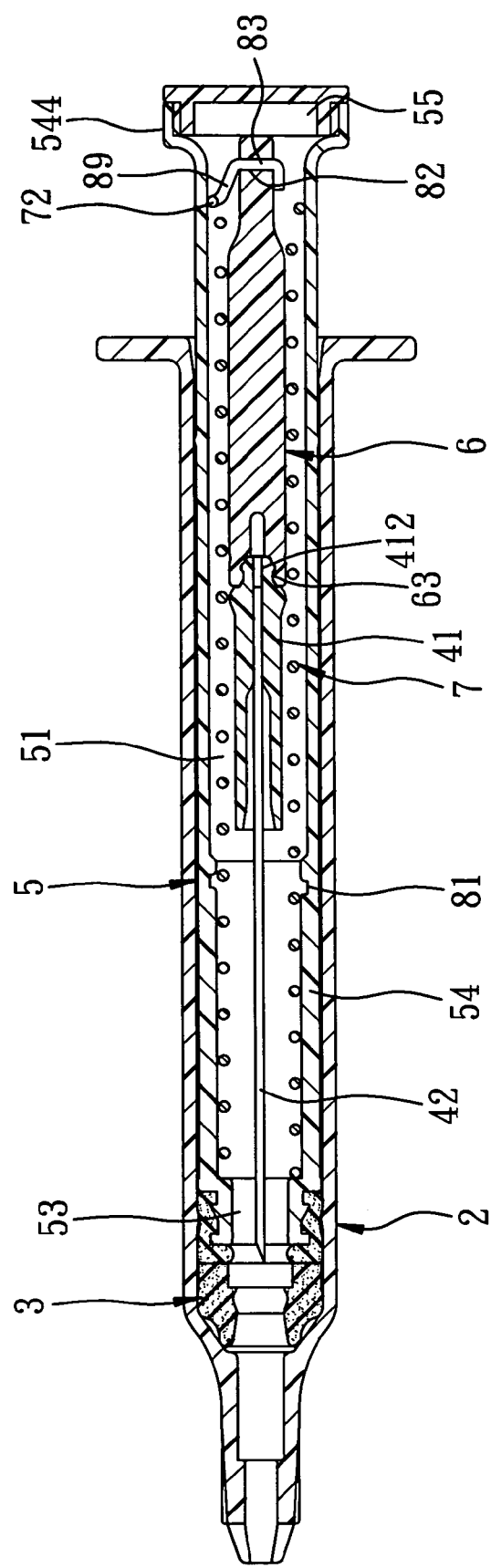
FIG. 8 is a sectional view of the first preferred embodiment in a retracted state.

Referring to FIGS. 7 and 8, when another force, i.e. the second external force, is applied to press the plunger body 5 to push the grip member 3 to the surrounding shoulder portion 26, the coupling rod 6 is prevented from movement due to the engagement of the central anchored area 63 with the anchoring portion 412, and the inner peripheral edge portion 545 is moved relative to the surrounding abutment area 66 such that the lower end 72 of the coiled spring 7 is brought to disengage from the retaining groove 81, thereby enabling the coupling rod 6 to be forced by virtue of the biasing action of the coiled spring 7 to move to the retracted position. At the same time, by engagement of the central anchored area 63 with the anchoring portion 412, the needle seat 41 and the needle cannula 42 can be retracted into the accommodation chamber 51, and can be retained in the accommodation chamber 51 by the end cap 55. Note that due to the dimension of the rear chamber segment 512 is larger than that of the front chamber segment 511, the way for the biasing member 7 is cleared when the biasing member 7 biases the coupling rod 6 towards the retracting position.

Figure 9:
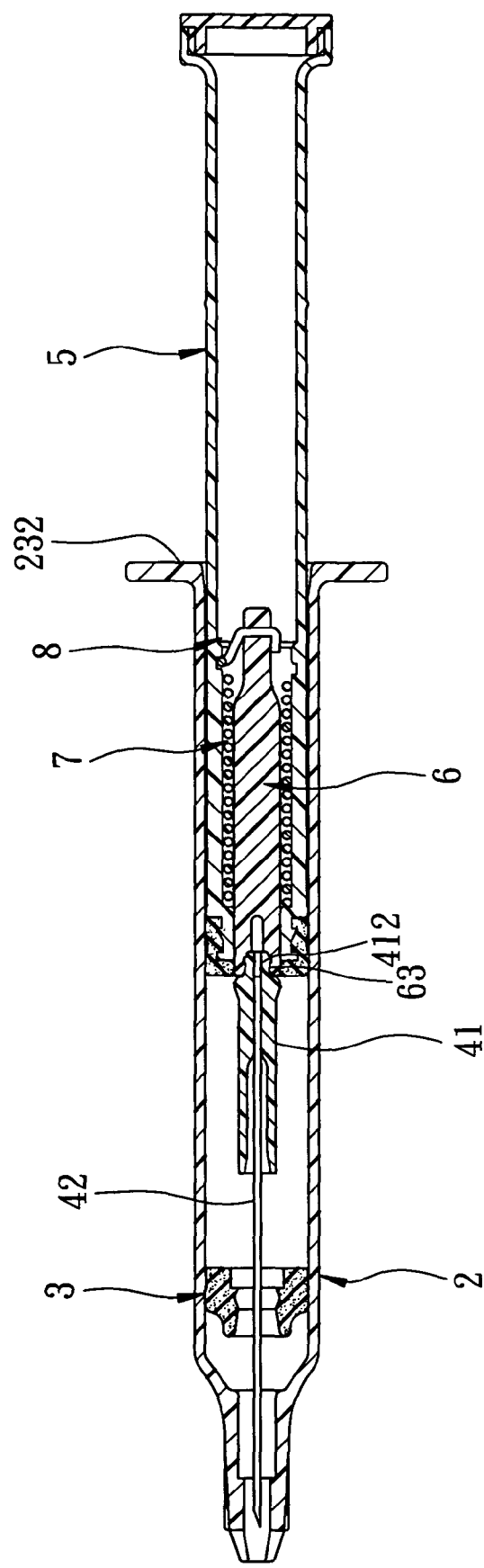
FIG. 9 is a sectional view of the first preferred embodiment in another retracted state.

Alternatively, referring to FIG. 9, the plunger body 5 may be pulled rearward after the engagement of the central anchored area 63 with the anchoring portion 412 so that the needle seat 41 and the needle cannula 42 can be retracted into the passage of the barrel 2 without using the biasing action of the coiled spring 7.

Figure 10:
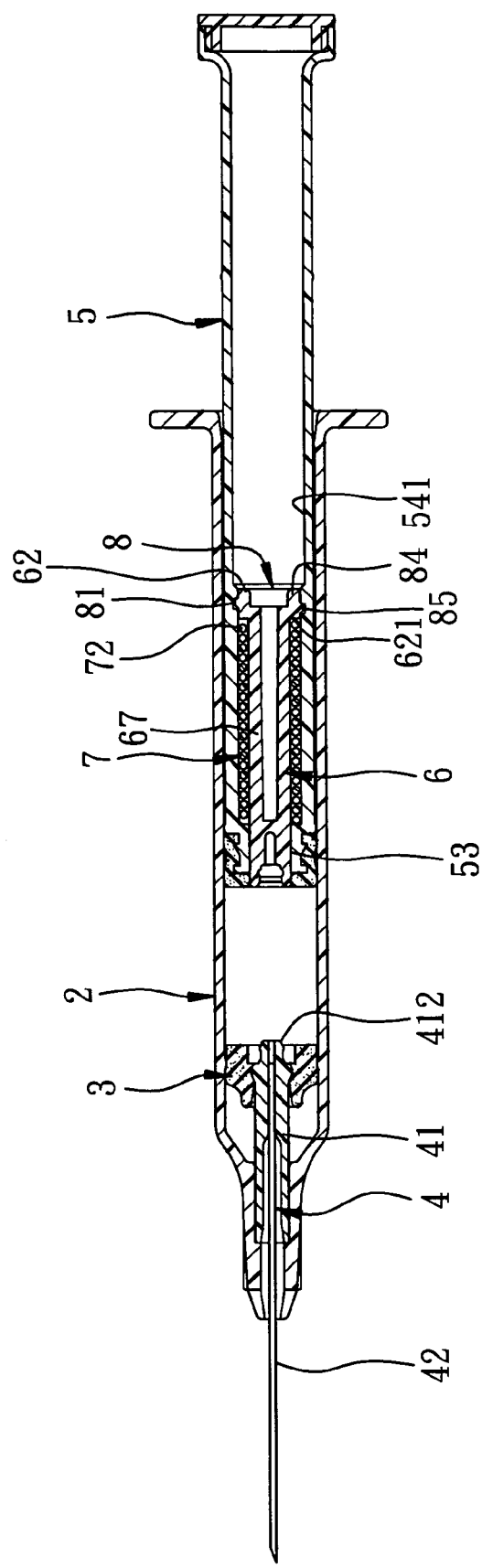
FIG. 10 is a sectional view of the second preferred embodiment of a disposable syringe according to this invention.
Figure 11:
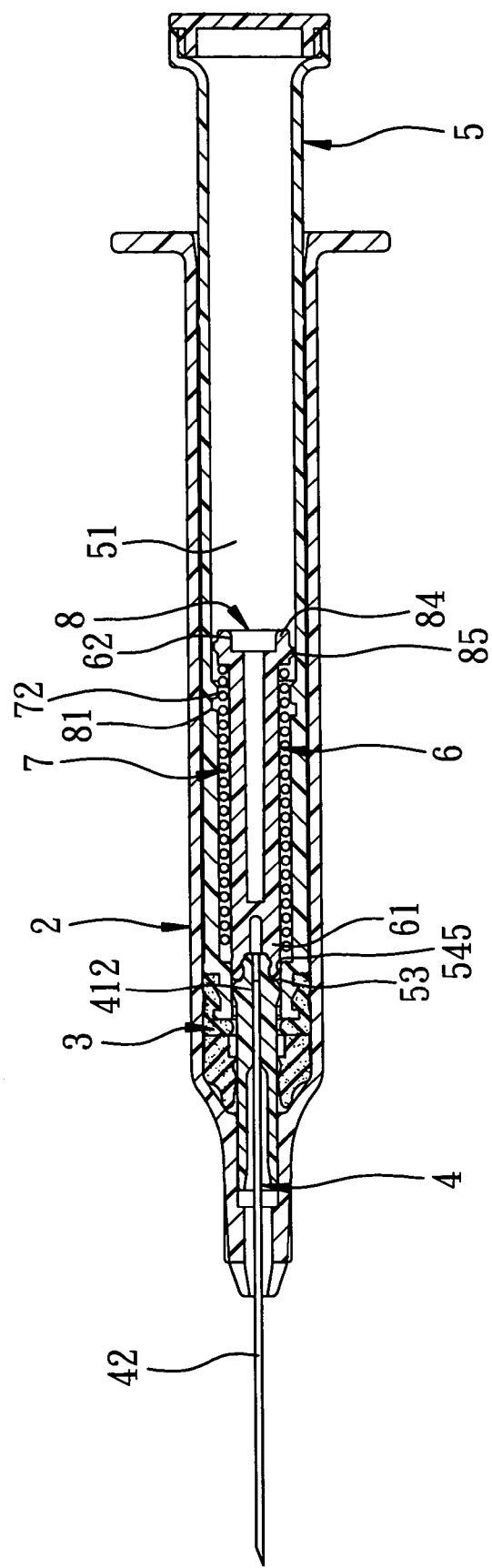
FIG. 11 is a sectional view of the second preferred embodiment, showing a tubular needle seat in a disengaging state.

Referring to FIGS. 10 and 11, the second preferred embodiment of a disposable syringe according to this invention is shown to be similar to the first preferred embodiment in construction. The differences reside in that the thrust end 62 of the coupling rod 6 has an enlarged end edge 84 which, in cooperation with the shank portion 67, forms an abutment shoulder 621 for engaging the lower end 72 of the coiled spring 7. The retaining member 8 further has a spirally surrounding protrusion 85 which is formed on and which extends radially from the enlarged end edge 84 so as to releasably engage the retaining groove 81 in the inner tubular wall surface 541 of the plunger body 5.

As such, when the anchoring portion 412 is pressed to move the upper coupling end 61 relative to the inner peripheral edge portion 545 by virtue of the second external force, the surrounding protrusion 85 is moved to disengage from the retaining groove 81 so as to permit retraction of the coupling rod 6, the needle seat 41 and the needle cannula 42 into the accommodation chamber 51.

Figure 12:
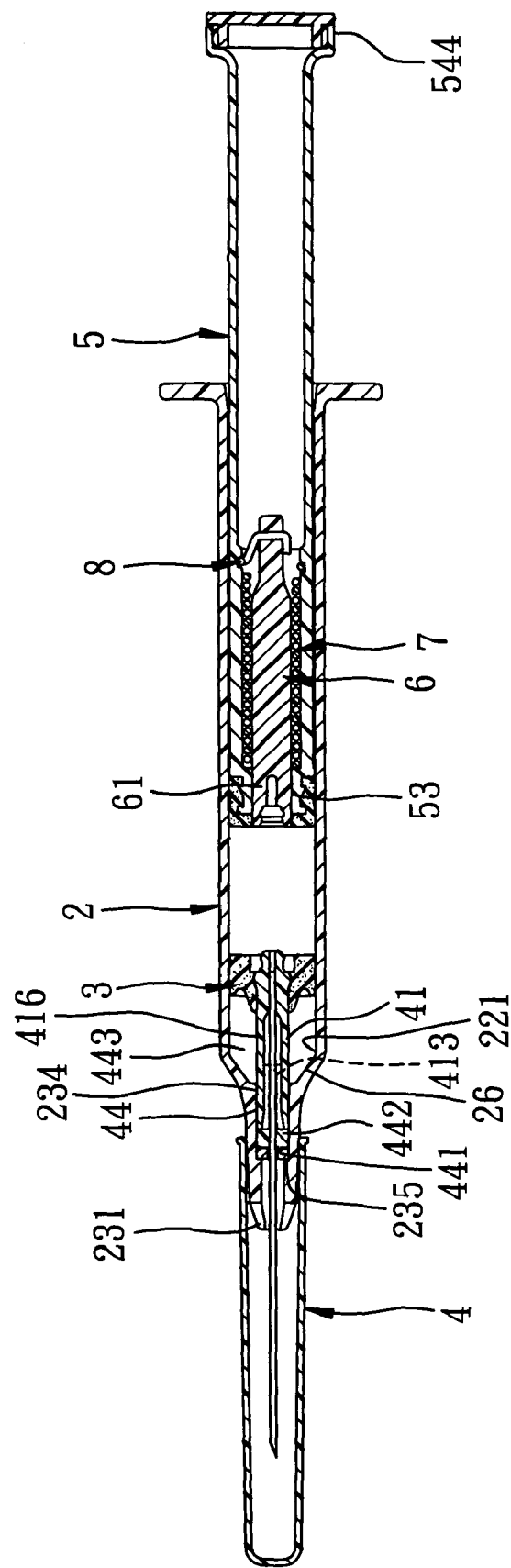
FIG. 12 is a sectional view of the third preferred embodiment of a disposable syringe according to this invention.
Figure 13:
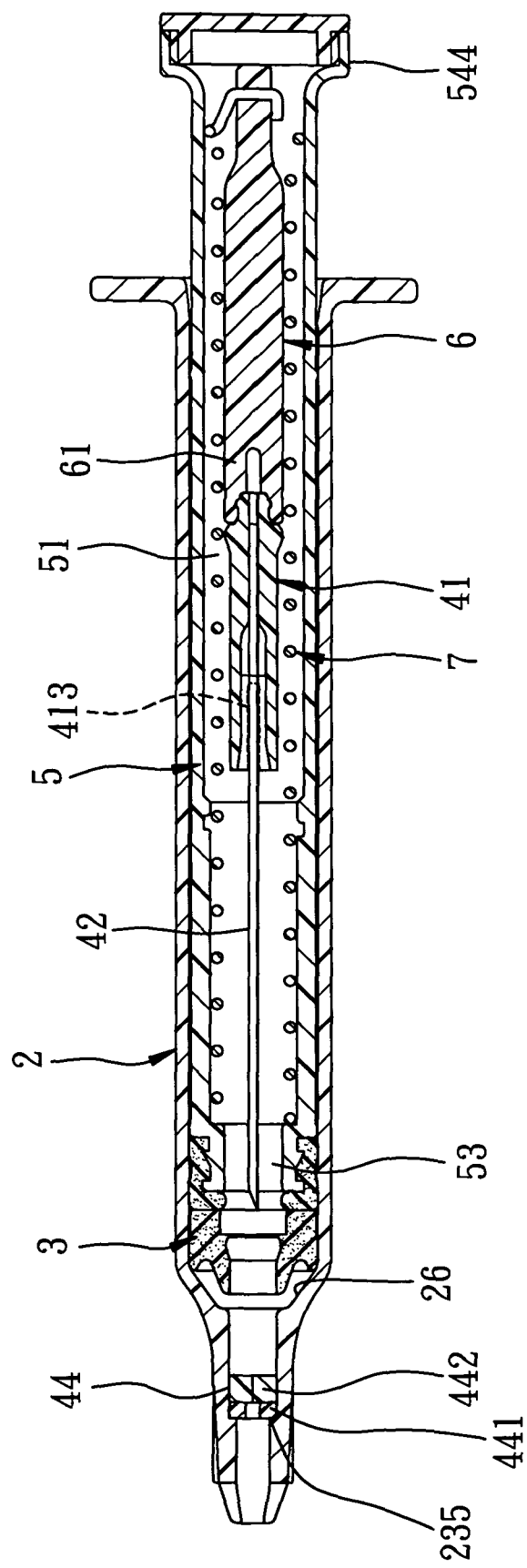
FIG. 13 is a sectional view of the third preferred embodiment in a retracted state.

Referring to FIGS. 12 and 13, the third preferred embodiment of a disposable syringe according to this invention is shown to be similar to the first preferred embodiment in construction, and further includes a sealing member 44 which is in air-tight engagement with the rear surrounding region 234 so as to cooperate with the grip member 3 to confine a compressible chamber 443 in the proximate surrounding region 221. The compressible chamber 443 is filled with a fluid. The sealing member 44 includes an elastomeric plate 441 and an elastomeric ring 442 which abut against each other. In addition, the hub portion 416 of the needle seat 41 has a through hole 413 which is formed therethrough and which is in fluid communication with the compressible chamber 443 such that when the grip member 3 is moved towards the surrounding shoulder portion 26, the fluid is forced to flow into the through hole 413 to assist in depression of the upper coupling end 61 of the coupling rod 6, as well as the needle seat 41 and the needle cannula 42, towards the bottom end wall 544, thereby speeding up the movement of the coupling rod 6 to the retracted position.

Figure 14:
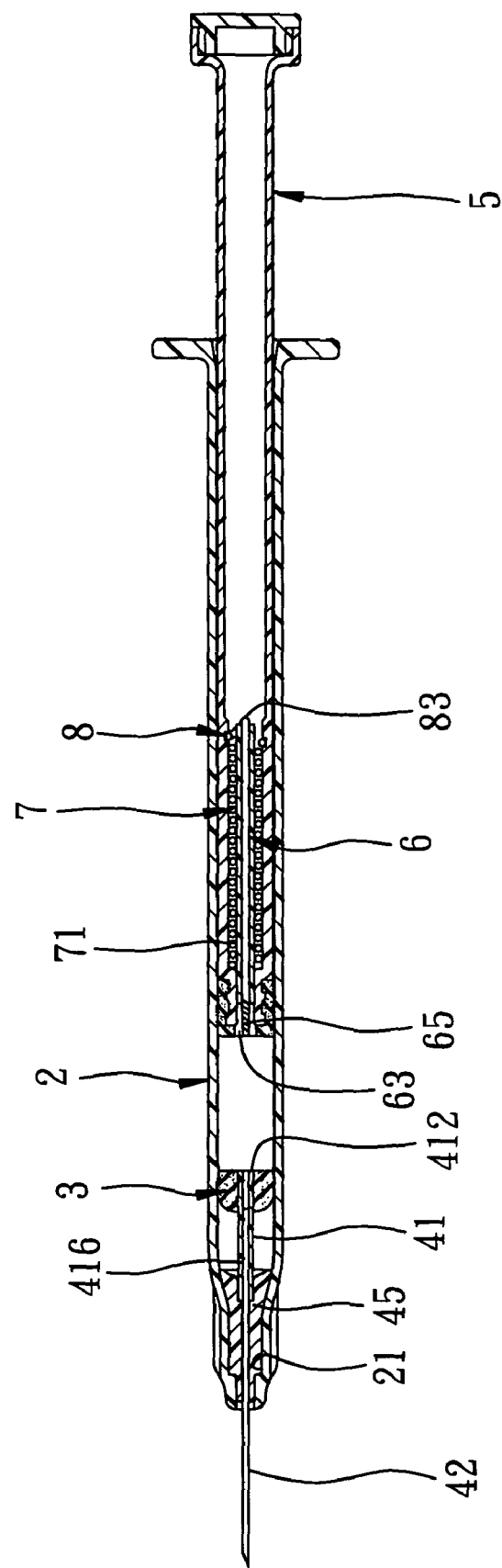
FIG. 14 is a sectional view of the fourth preferred embodiment of a disposable syringe according to this invention.
Figure 16:
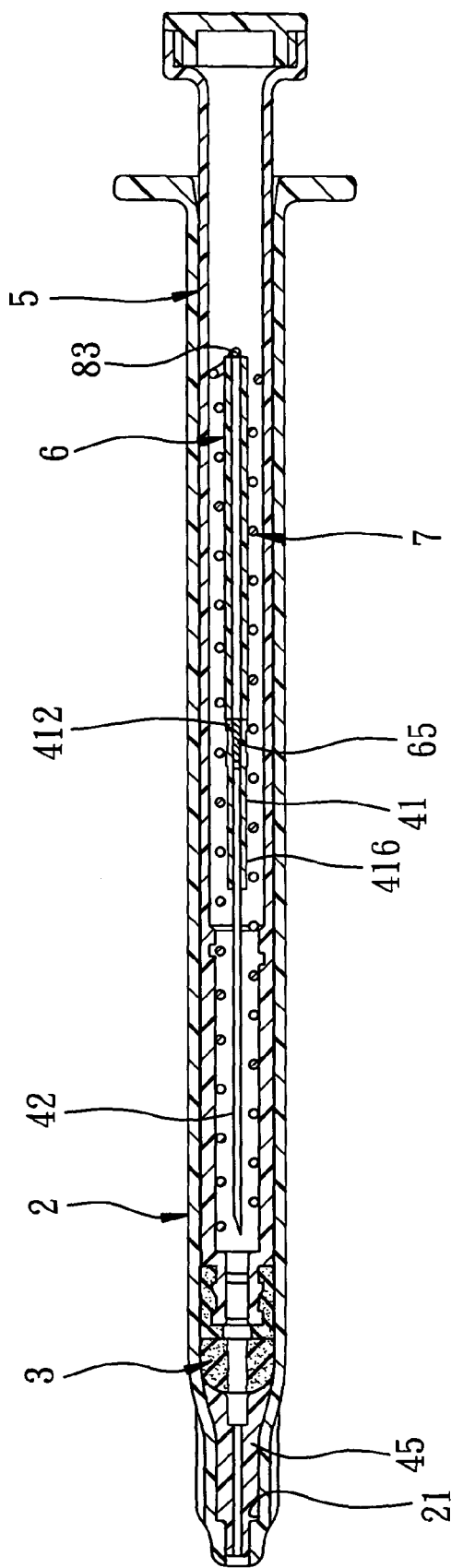
FIG. 16 is a sectional view of the fourth preferred embodiment in a retracted state.

Referring to FIGS. 14 and 16, the fourth preferred embodiment of a disposable syringe according to this invention is adapted for injecting medication of a very small volume, such as 1 ml. Thus, the barrel 2, the grip member 3, the needle seat 41, the plunger body 5, the coupling rod 6, the biasing member 7 and the retaining member 8 are comparatively smaller in size. In addition, an embossed pin 65 extends from the pushed end 83 forwardly, projects forwardly of the central anchored area 63 of the coupling rod 6, and is formed with screw threads thereon. The embossed pin 65 extends toward the anchoring portion 412 of the needle seat 41 for insertion thereinto and for retention therein, thereby providing the holding force.

Figure 15:
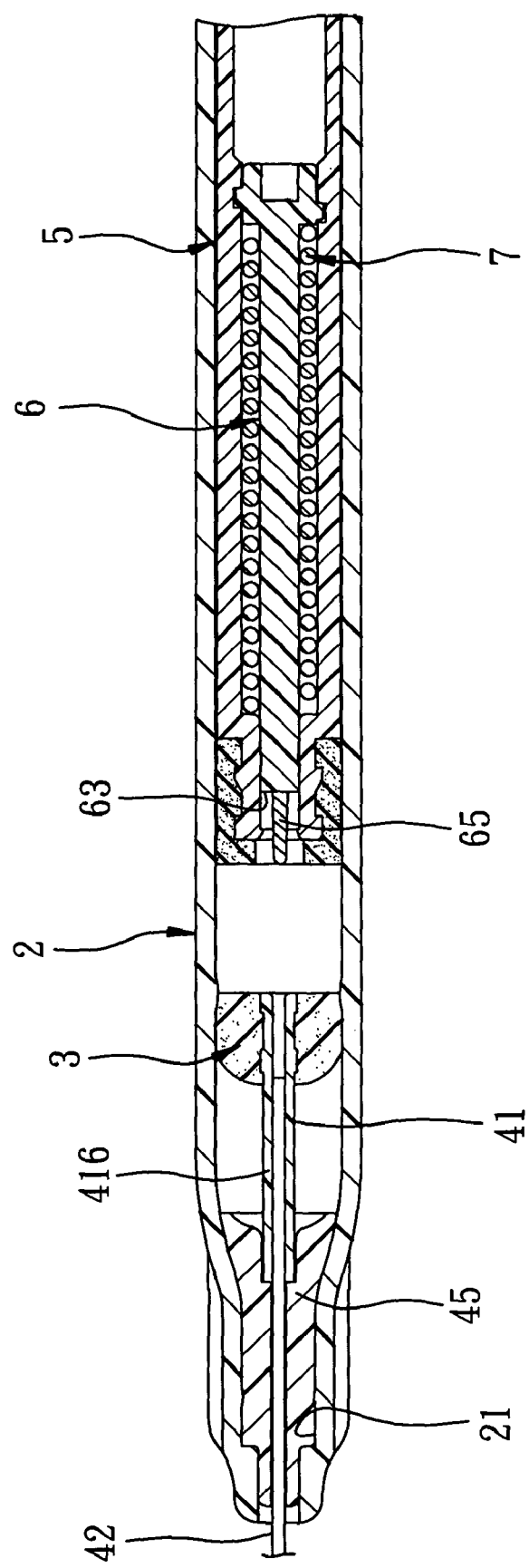
FIG. 15 is a fragmentary sectional view showing an alternative configuration of a tubular needle seat and a coupling rod of the fourth preferred embodiment.

Alternatively, referring to FIG. 15, the embossed pin 65 is also formed on and extends from the central anchored area 63 of the coupling rod 6.

Furthermore, a needle mount 45 is provided to sleeve on and to secure the needle cannula 42 and the hub portion 416 of the needle seat 41. An assembly of the needle mount 45, the needle cannula 42 and the needle seat 41 is inserted into the barrel 2. Thus, mounting of the needle cannula 42 and the needle seat 41 to the barrel 2 can be conducted easily, and the smaller-diameter segment 21 of the barrel 2 can have a relatively large diameter so as to facilitate fabrication.

Figure 17:
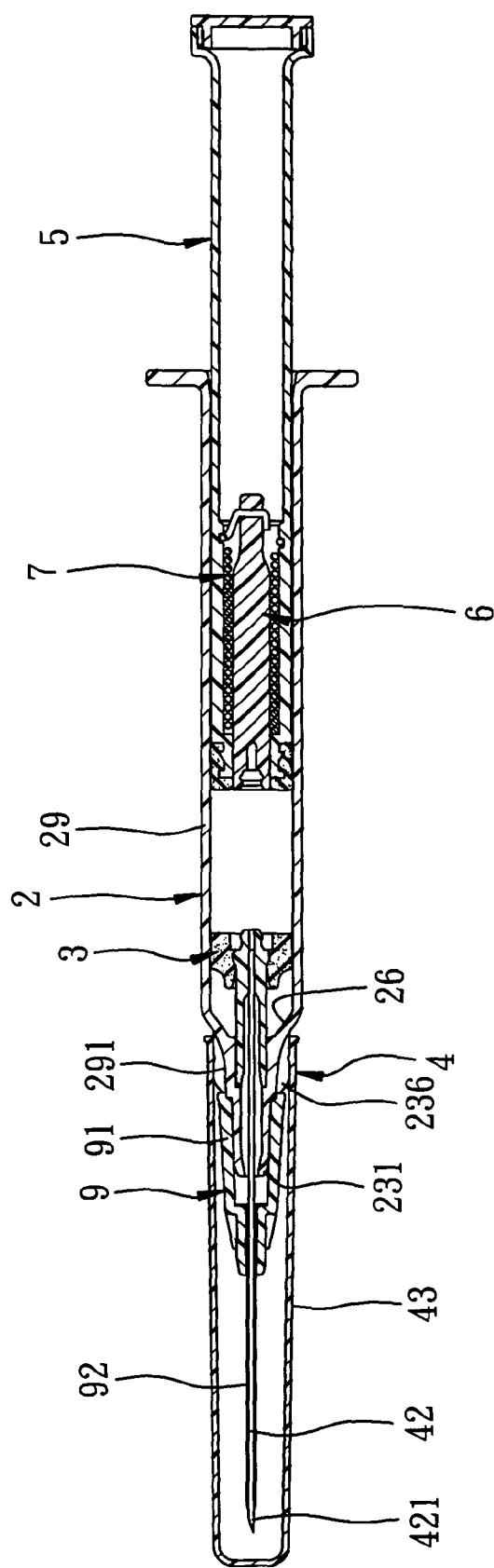
FIG. 17 is a sectional view of the fifth preferred embodiment of a disposable syringe according to this invention.
Figure 18:
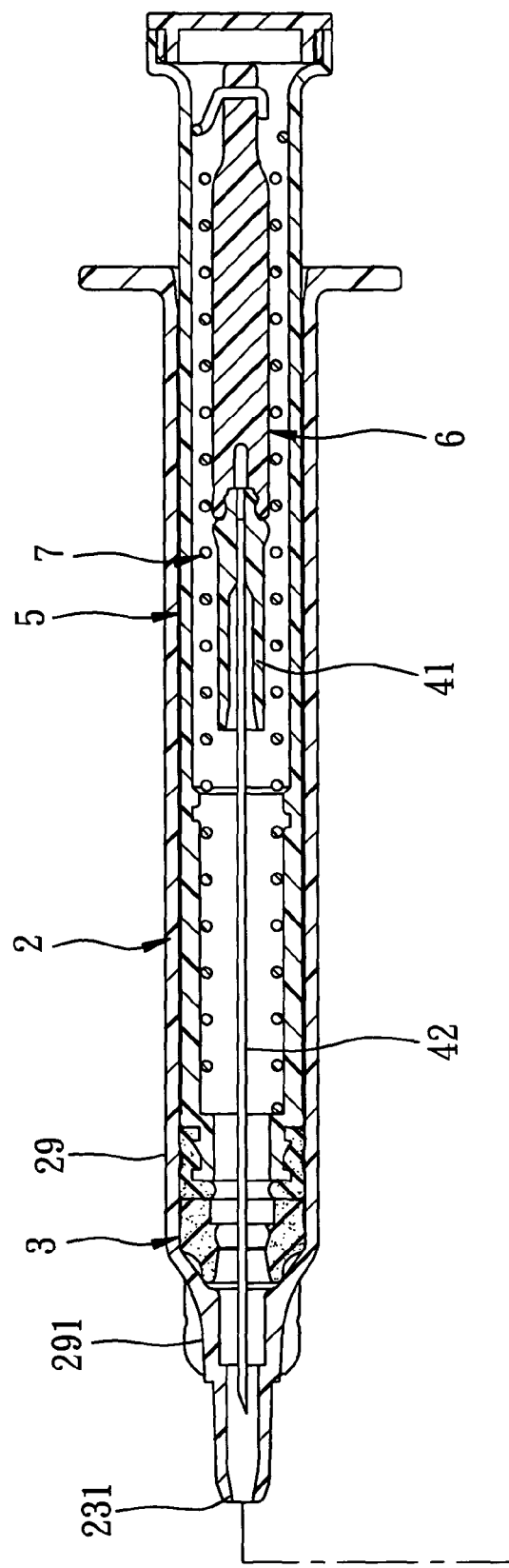
FIG. 18 is an exploded sectional view of the fifth preferred embodiment in a retracted state.
Figure 18:
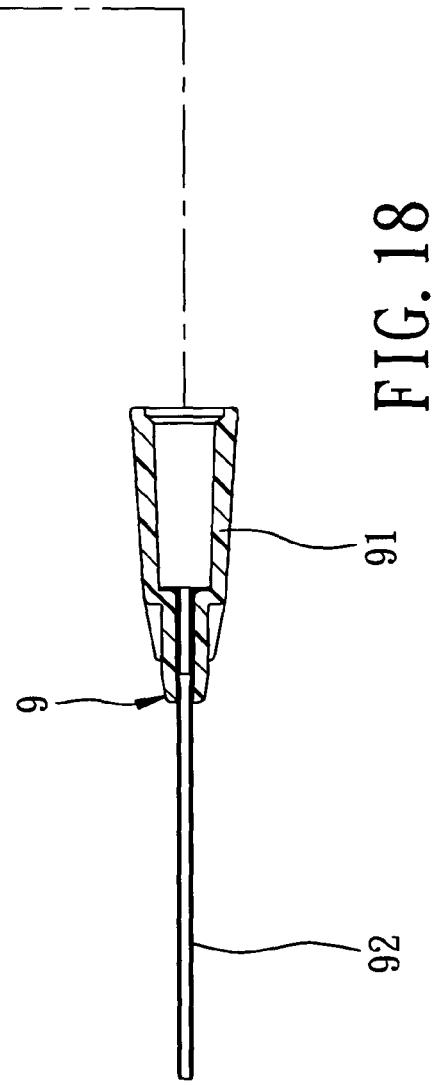

Referring to FIGS. 17 and 18, the fifth preferred embodiment of a disposable syringe according to this invention is shown to be similar to the first preferred embodiment in construction, and further includes an intravenous catheter device 9 which includes a catheter hub 91 and a tubular catheter 92. The catheter hub 91 defines a duct therein, and includes a sleeve portion that is sleeved on the outer surrounding barrel wall surface 29 of the barrel 2 adjacent to the open upper end 231, and a tip portion opposite to the sleeve portion along the axis. The tubular catheter 92 has a proximate segment which is disposed in the tip portion of the catheter hub 91 and which extends along the axis to communicate fluidly with the duct, and a distal segment that extends from the proximate segment along the axis to project outwardly of the tip portion. The needle cannula 42 extends through the tubular catheter 92 to terminate at a tip end 421 that projects outwardly of the distal segment of the tubular catheter 92.

In use, when the tip end 421 and the distal segment of the tubular catheter 92 are inserted into a patient's vein, the user can pull the plunger body 5 slightly rearward to draw blood so as to confirm correct insertion of the tubular catheter 92 into the patient's vein. After the needle cannula 42 is removed from the tubular catheter 92, the needle seat 41 and the needle cannula 42 are retracted into the plunger body 5 in the same manner as described above.

Figure 19:
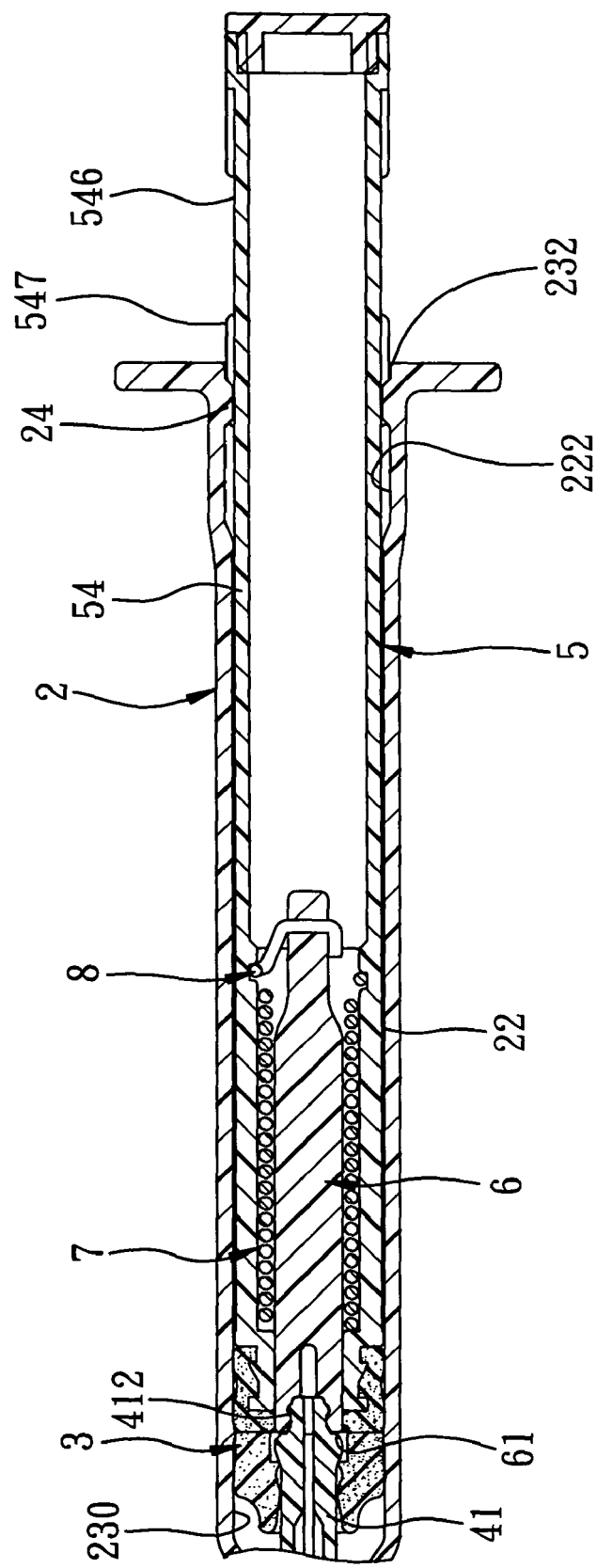
FIG. 19 is a fragmentary sectional view of the sixth preferred embodiment of a disposable syringe according to this invention.

Referring to FIG. 19, the sixth preferred embodiment of a disposable syringe according to this invention is shown to be similar to the fifth preferred embodiment in construction, and further includes a first male screw thread segment 547 and a first female screw thread segment 24 which are respectively disposed on the outer tubular wall surface 546 of the plunger body 5 and the distal surrounding region 222 of larger-diameter segment 22 of the barrel 2. When the first male screw thread segment 547 is in a screw-in engagement with the first female screw thread segment 24 to provide the second external force, the plunger body 5 can be moved more easily to push the grip member 3 to the surrounding shoulder portion 26.

Figure 20:
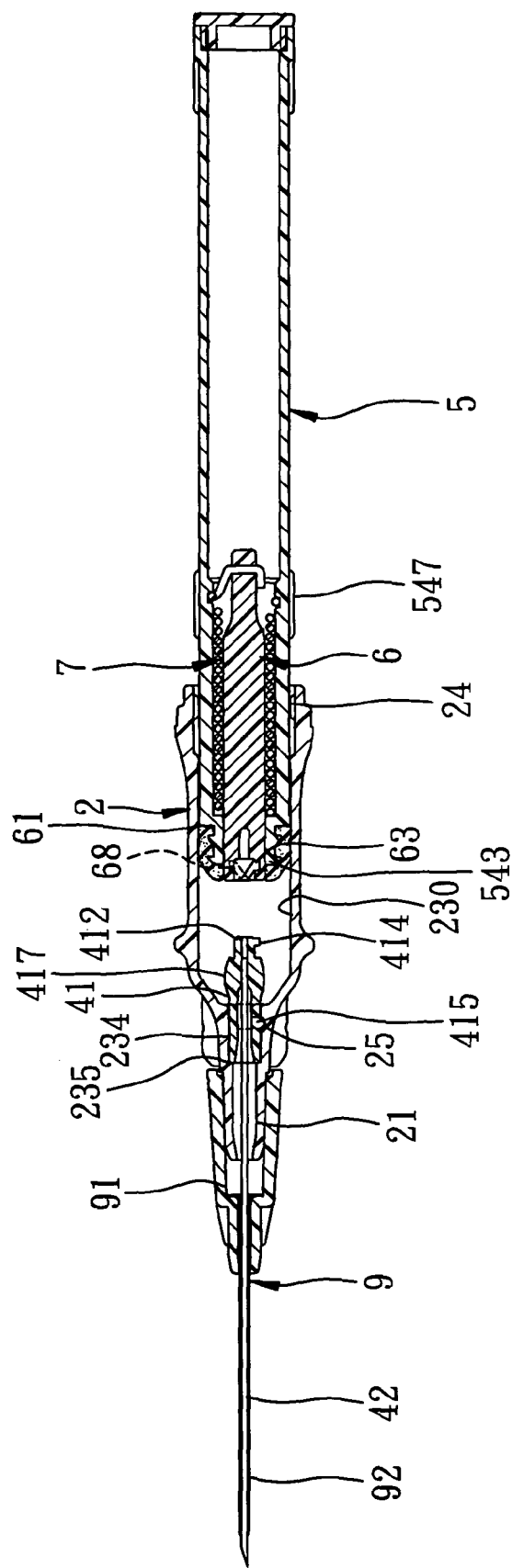
FIG. 20 is a sectional view of the seventh preferred embodiment of a disposable syringe according to this invention.

Referring to FIG. 20, the seventh preferred embodiment of a disposable syringe according to this invention is shown to be similar to the sixth preferred embodiment in construction. The differences reside in that the grip member includes a second female screw thread segment 25 which is disposed on the rear surrounding region 234 of the smaller-diameter segment 21 of the barrel 2, and a second male screw thread segment 415 which is disposed on the surrounding gripped portion 417 of the needle seat 41. The second male screw thread segment 415 is in a threaded engagement with the second female screw thread segment 25 such that the resisting force is provided between the surrounding gripped portion 417 and the rear surrounding region 234, and such that screw-out movement of the second male screw thread segment 415 relative to the second female screw thread segment 25 results in disappearance of the resisting force to permit disengagement of the surrounding gripped portion 417 from the rear surrounding region 234.

In addition, the central anchored area 63 has a third female screw thread segment 68 which is disposed in the engaging recess thereof. The anchoring portion 412 has a third male screw thread segment 414. The anchoring portion 412 is brought into engagement with the central anchored area 63 by virtue of rotation of the third male screw thread segment 414 and the third female screw thread segment 68 relative to each other, thereby providing the holding force.

Figure 21:
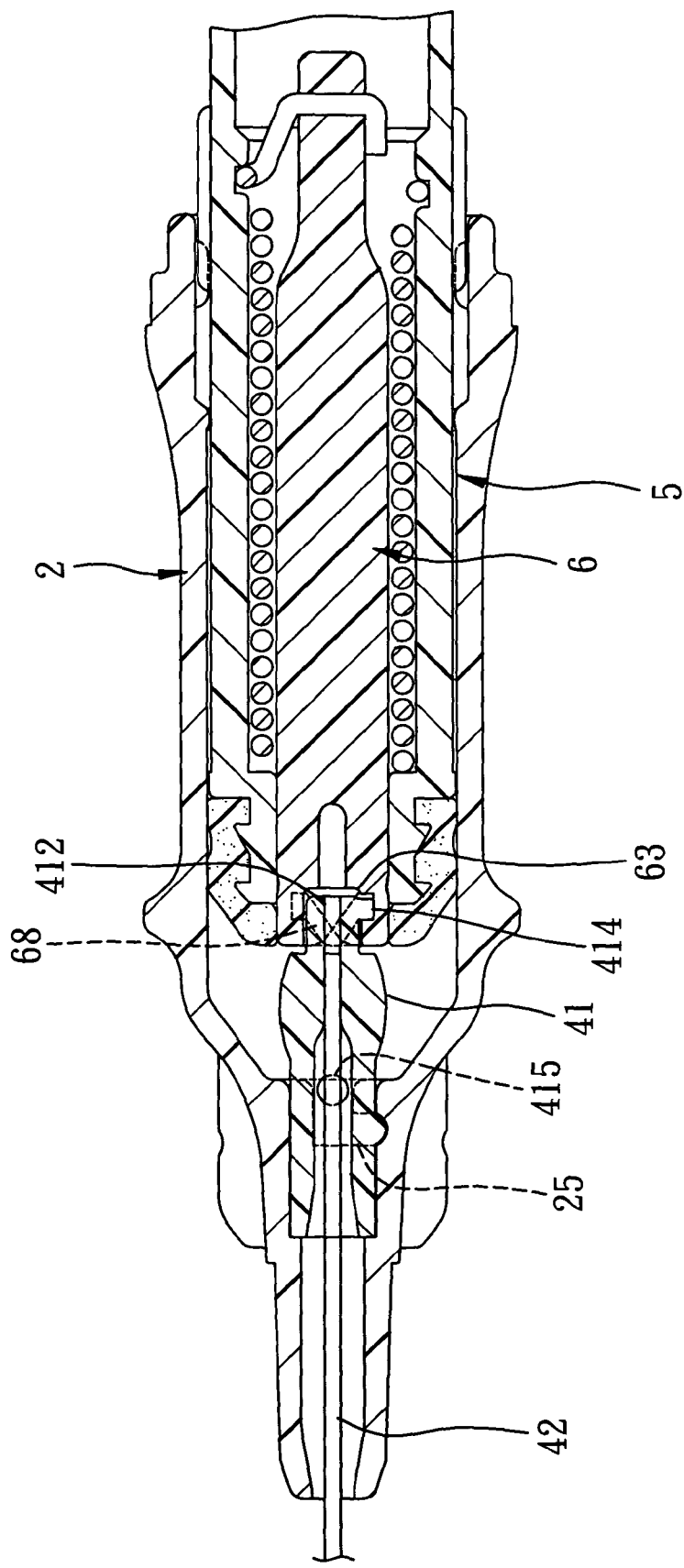
FIGS. 21 and 22 are fragmentary sectional views showing a grip member of the seventh preferred embodiment in two different states.
Figure 22:
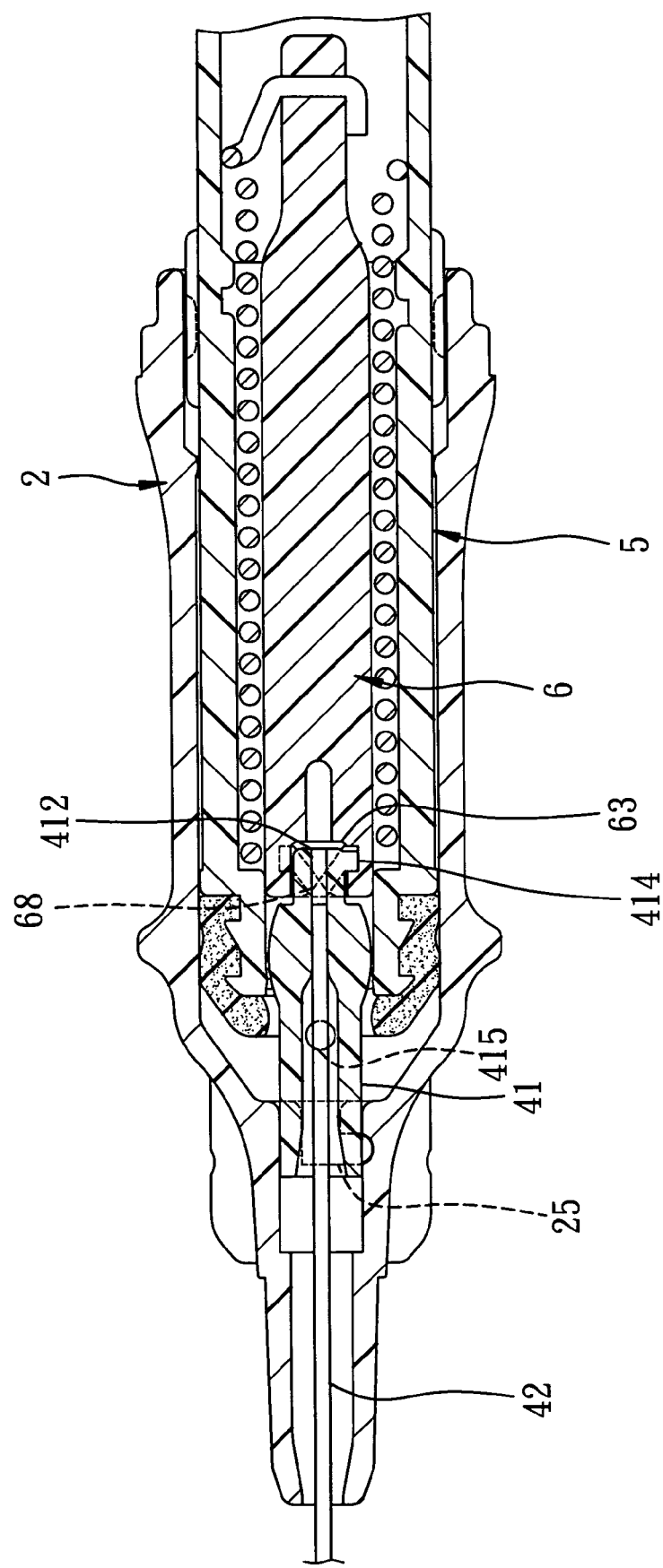
Figure 23:
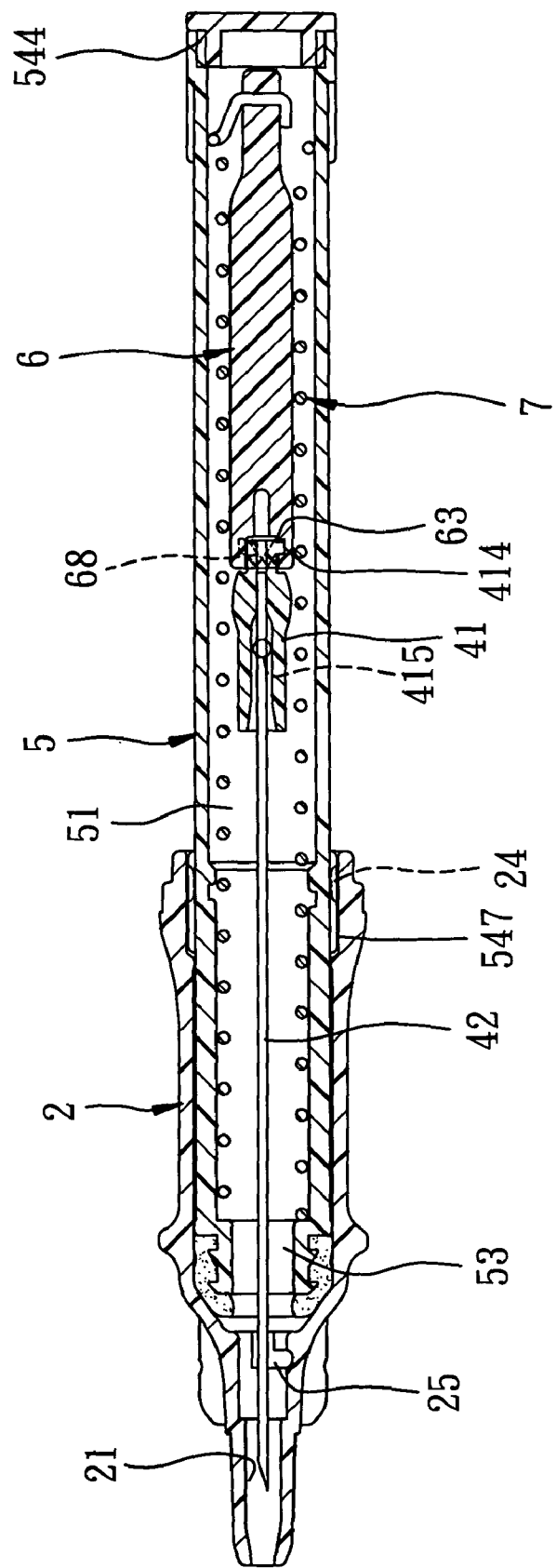
FIG. 23 is a sectional view of the seventh preferred embodiment in a retracted state.

As such, referring to FIGS. 20 to 22, when the plunger body 5 is rotated by virtue of the screw-in engagement of the first male screw thread segment 547 and the first female screw thread segment 24, the third female screw thread segment 68 is permitted to engage the third male screw thread segment 414, and the second male screw thread segment 415 is permitted to disengage from the second female screw thread segment 25 such that the coupling rod 6 is pressed as described above to permit retraction of the needle seat 41 and the needle cannula 42 into the plunger body 5.

Figure 24:
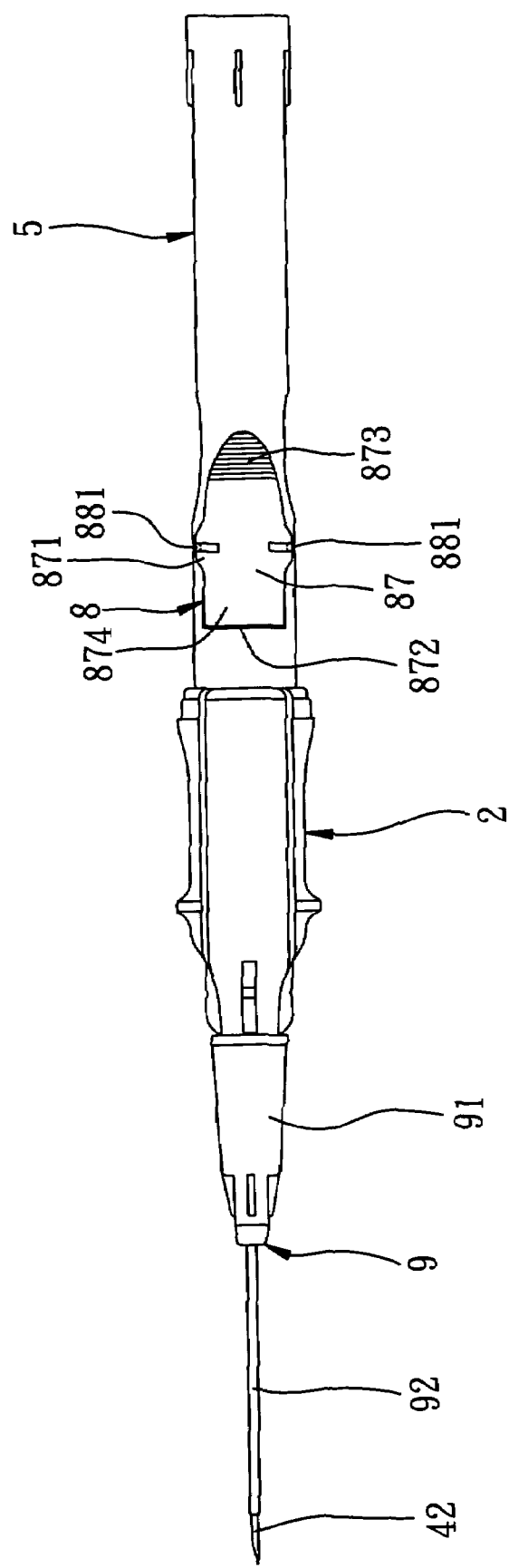
FIG. 24 is a side view of the eighth preferred embodiment of a disposable syringe according to this invention.
Figure 25:
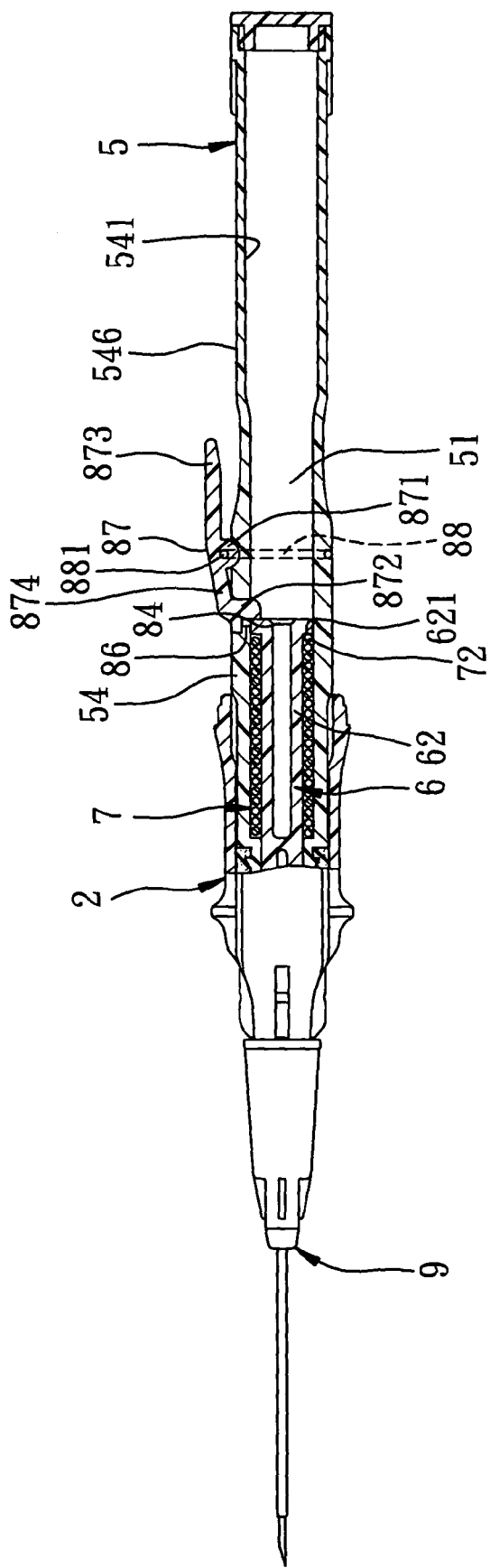
FIG. 25 is a partly sectional view of the eighth preferred embodiment.

Referring to FIGS. 24 and 25, the eighth preferred embodiment of a disposable syringe according to this invention is shown to be similar to the seventh preferred embodiment in construction. The differences reside in that the thrust end 62 of the coupling rod 6 has an enlarged end edge 84 which, in cooperation with the shank portion 67, forms an abutment shoulder 621 for engaging the lower end 72 of the coiled spring 7. The outer tubular wall surface 546 of the tubular intermediate wall 54 of the plunger body 5 has an access hole 86 which extends radially through the inner tubular wall surface 541.

Figure 26:
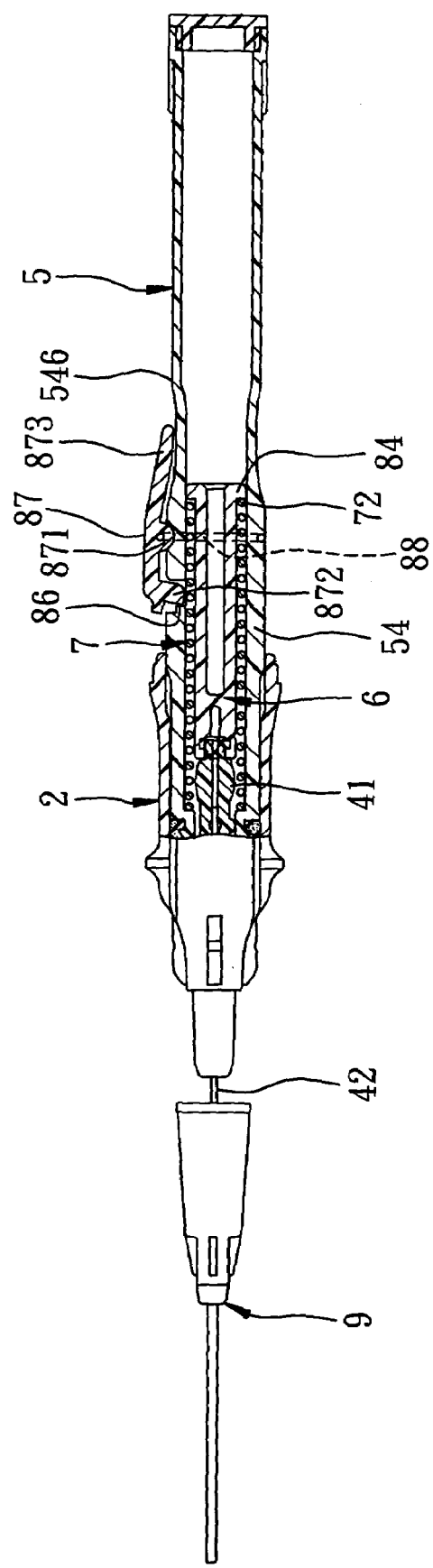
FIG. 26 is a partly sectional view of the eighth preferred embodiment in a retracted state.

In addition, the retaining member 8 has a locking pin 872 which is received in the access hole 86 and which is movable radially between a locking position (see FIG. 25), where the locking pin 872 extends into the accommodation chamber 51 to abut the enlarged end edge 84 against the biasing action of the coiled spring 7, and a releasing position (see FIG. 26), where the locking pin 872 is retracted to release the enlarged end edge 84 so that the coupling rod 6 is forced by virtue of the biasing action of the coiled spring 7 to move to the retracted position.

Furthermore, the triggering member is formed as a lever 87, and is mounted pivotally on the outer tubular wall surface 546 at a fulcrum point 871 by means of a C-shaped clip 88 which is sleeved on the outer tubular wall surface 546 and which has an end 881 passing through the fulcrum point 871. The lever 87 includes a weight end 874 which is formed integrally with the locking pin 872, and a power end 873 which is disposed at the opposite side of the weight end 874 relative to the fulcrum point 871 so as to be actuated to move the locking pin 872 to the releasing position.

Figure 27:
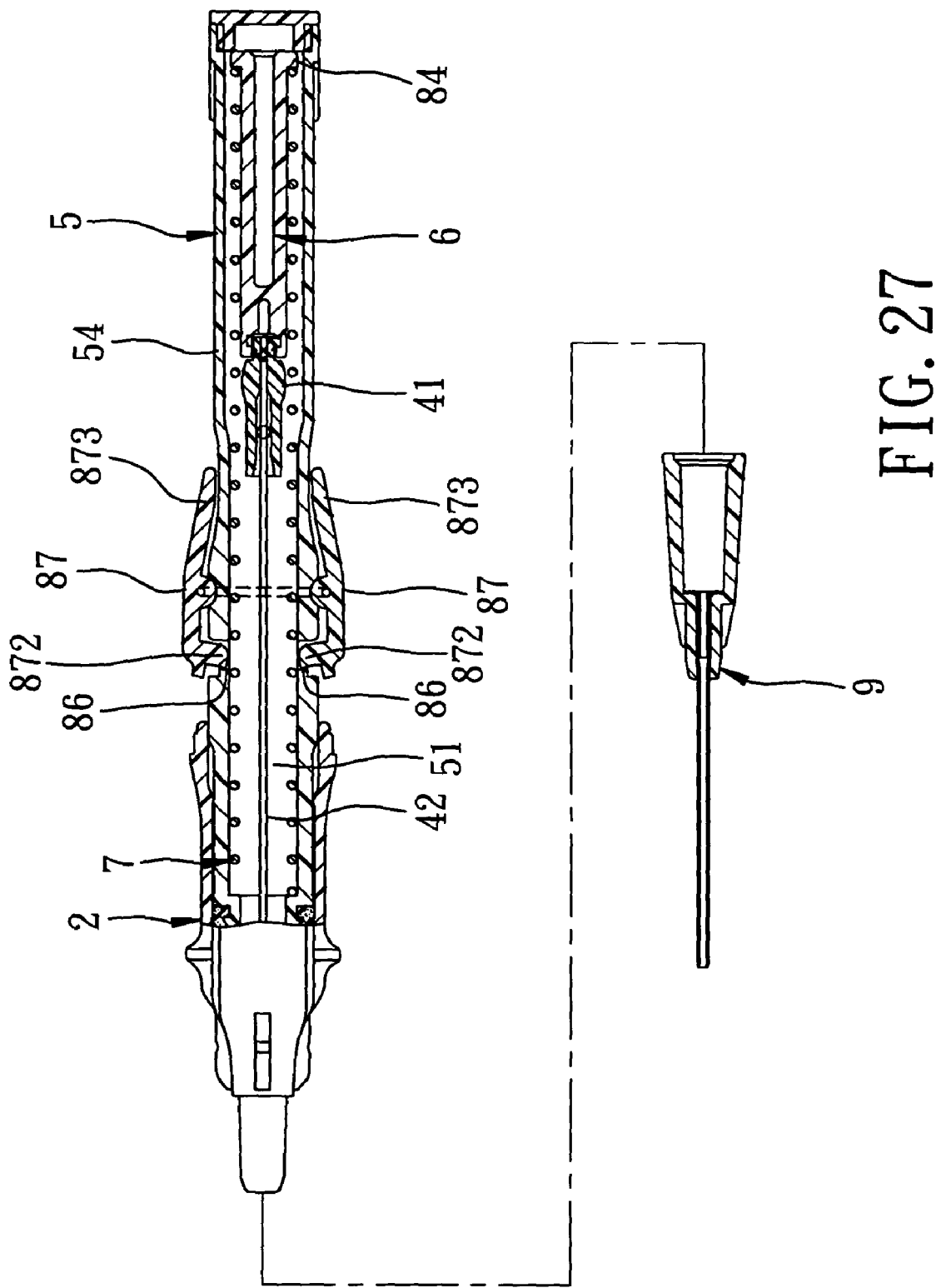
FIG. 27 is an exploded, partly sectional view of the ninth preferred embodiment of a disposable syringe according to this invention.

Referring to FIG. 27, alternatively, in the ninth preferred embodiment, the tubular intermediate wall 54 of the plunger body 5 has two access holes 86, the retaining member 8 has two locking pins 872, and the triggering member has two levers 87 which are mounted pivotally on the tubular intermediate wall 54 by means of a C-shaped clip 88. Pressing of the power ends 873 of the levers 87 can result in retraction of the locking pins 872 to permit retracting movement of the coupling rod 6 by virtue of the biasing action of the coiled spring 7.

As illustrated, the disposable syringe of this invention has the following advantages:

1. After completion of the injection course, the first and second external forces are applied to push the plunger body 5 forward to permit disengagement of the surrounding gripped portion 417 of the needle seat 41 from a respective one of the rear surrounding region 234 and the proximate surrounding region 221, to permit engagement of the anchoring portion 412 with the central anchored area 63, and to permit retraction of the needle seat 41 and the needle cannula 42 into the plunger body 5, thereby rendering the disposal of the syringe safe and convenient.

2. Since the coupling rod 6 is in air-tight engagement with the inner peripheral edge portion 545 of the plunger body 5, entry of medication fluid into the plunger body 5 can be prevented. In addition, the disposable syringe has a simple construction that is easy to fabricate and assemble at a relatively low cost.

3. The disposable syringe can serve as an intravenous catheter inserting device for insertion of the tubular catheter 92 into a patient's vein for administrating medication fluid into the patient's vein or for drawing blood.

While the present invention has been described in connection with what is considered the most practical and preferred embodiments, it is understood that this invention is not limited to the disclosed embodiments but is intended to cover various arrangements included within the spirit and scope of the broadest interpretations and equivalent arrangements.

We claim:

1. A disposable syringe comprising:
   a needle cannula;
   a barrel having an inner surrounding barrel wall surface which surrounds an axis and which confines a passage, said passage having open lower and upper ends which are disposed opposite to each other in a longitudinal direction parallel to the axis, said inner surrounding barrel wall surface including a larger-diameter segment and a smaller-diameter segment which confine rear and front passageways respectively, and which are disposed proximate to said open lower and upper ends, respectively, to form a surrounding shoulder portion therebetween, said smaller-diameter segment including a front surrounding region and a rear surrounding region which is proximate to said surrounding shoulder portion, said larger-diameter segment including proximate and distal surrounding regions which are opposite to each other in the longitudinal direction and which are respectively proximate to and distal from said surrounding shoulder portion;
   a tubular needle seat including
      a hub portion disposed to fix said needle cannula therein, and having a surrounding front end wall extending radially relative to the axis,
      a surrounding gripped portion extending from said hub portion in the longitudinal direction and away from said surrounding front end wall, and
      an anchoring portion extending from said surrounding gripped portion in the longitudinal direction and away from said hub portion;
   a grip member disposed to bring said surrounding gripped portion into engagement with one of said rear surrounding region and said proximate surrounding region, said grip member being configured to provide a resisting force that holds said surrounding gripped portion in position so as to prevent movement of said surrounding gripped portion relative to a respective one of said rear surrounding region and said proximate surrounding region during a piercing action of said needle cannula for a hypodermic or intravenous injection, and that permits disengagement of said surrounding gripped portion from said respective one of said rear surrounding region and said proximate surrounding region so as to enable a subsequent movement of said tubular needle seat relative to said inner surrounding barrel wall surface when said grip member is subjected to a first external force;

a plunger which, in a position of use, is disposed to be movable in said larger-diameter segment, said plunger including a plunger body which includes a top end wall movable towards said anchoring portion, a bottom end wall opposite to said top end wall in the longitudinal direction, and extending outwardly of said open lower end so as to be manually operable, and a tubular intermediate wall that is interposed between said top and bottom end walls, and that confines an accommodation chamber, said top end wall having an inner peripheral edge portion that surrounds the axis, and that defines an access opening therein, which is communicated with said accommodation chamber, and a coupling rod including an upper coupling end which is inserted in said access opening, and which has a central anchored area that is engageable with said anchoring portion by a holding force such that the engagement of said central anchored area with said anchoring portion is not disrupted during the disengagement of said surrounding gripped portion from said respective one of said rear surrounding region and said proximate surrounding region, and a surrounding abutment area that surrounds said central anchored area, and that is disposed to be in frictional engagement with said inner peripheral edge portion, such that when said upper coupling end is depressed towards said bottom end wall by virtue of movement of said tubular needle seat relative to said upper coupling end, said coupling rod is disengaged from said inner peripheral edge portion so as to enable said coupling rod to be forced from the position of use to a retracted position where said coupling rod is disposed closer to said bottom end wall, and a shank portion extending from said upper coupling end towards said bottom end wall and terminating at a thrust end;

a biasing member disposed between said shank portion and said tubular intermediate wall to bias said coupling rod towards the retracted position;

a retaining member disposed to retain said thrust end in the position of use against biasing action of said biasing member; and a triggering member disposed to prevent said retaining member from retaining said thrust end in response to a second external force, thereby permitting said coupling rod to be biased towards the retracted position.

2. The disposable syringe according to claim 1, wherein said proximate surrounding region is formed with a retaining protrusion, said grip member including an outer grip wall surface which is configured to engage retainingly said retaining protrusion with a first frictional force and which is in water-tight engagement with said proximate surrounding region, and an inner grip wall surface which is opposite to said outer grip wall surface in radials direction relative to the axis and which engages retainingly said surrounding gripped portion with a second frictional force that, together with the first frictional force, serves as the resisting force.

3. The disposable syringe according to claim 2, wherein said smaller-diameter segment has a shoulder disposed between said front and rear surrounding regions to block forward movement of said surrounding front end wall so as to permit disengagement of said surrounding grip portion from said inner grip wall surface and from said proximate surrounding region when said top end wall is moved to push said grip member towards said surrounding shoulder portion by the first external force that is greater than the resisting force, thereby enabling the engagement of said central anchored area with said anchoring portion.

4. The disposable syringe according to claim 3, wherein said central anchored area has an embossed pin which extends toward said anchoring portion so as for insertion thereinto and for retention therein, thereby providing the holding force.

5. The disposable syringe according to claim 2, further comprising a sealing member which is in air-tight engagement with said rear surrounding region so as to cooperate with said grip member to confine a compressible chamber in said proximate surrounding region, said compressible chamber being filled with a fluid, said hub portion of said needle seat having a through hole which is formed therethrough to be in fluid communication with said compressible chamber such that when said grip member is moved towards said surrounding shoulder portion, said fluid is forced to flow into said through hole to assist in depression of said upper coupling end towards said bottom end wall, thereby speeding up movement of said coupling rod to the retracted position.

6. The disposable syringe according to claim 2, further comprising a first male screw thread segment and a first female screw thread segment which are respectively disposed on said outer tubular wall surface and said distal surrounding region for providing the second external force by virtue of screw-in engagement of said first male screw thread segment with said first female screw thread segment.

7. The disposable syringe according to claim 1, wherein said barrel has an outer surrounding barrel wall surface which surrounds the axis and which includes front and rear outer surrounding segments that are disposed opposite to said smaller-diameter segment and said larger-diameter segment in directions radial to the axis, respectively, and a rib portion which is disposed on said front outer surrounding segment and which extends in the longitudinal direction, said disposable syringe further comprising a tip protector which is sleeved frictionally on said rib portion so as for shielding said needle cannula.

8. The disposable syringe according to claim 7, wherein said outer surrounding barrel wall surface further includes a transition surrounding segment which is interposed between said front and rear outer surrounding segments, and which diverges gradually from said front outer surrounding segment to said rear outer surrounding segment such that extension of said rib portion onto said transition surrounding segment ensures a firm engagement between said tip protector and said rib portion when said tip protector is brought to be sleeved thereonto.

9. The disposable syringe according to claim 1, wherein said tubular intermediate wall has outer and inner tubular wall surfaces opposite to each other in radial directions relative to the axis, said retaining member having a retaining groove which is formed in said inner tubular wall surface, which extends radially and towards said outer tubular wall surface, and which is displaced from said top end wall, said biasing member being a coiled spring that surrounds said shank portion, said coiled spring having an upper end engaging said top end wall, and a lower end that is opposite to said upper end, said lower end being inserted into and being retained in said retaining groove against the biasing action, said triggering member including an actuated portion which has a pushed end coupled to and moved with said thrust end, and a pulling end disposed to pull said lower end out of said retaining groove once said pushed end is moved downwardly with said thrust end when said upper coupling end is depressed to be disengaged from said inner peripheral edge, thereby enabling said coupling rod to be forced by virtue of the biasing action to move to the retracted position.

10. The disposable syringe according to claim 1, wherein said biasing member is a coiled spring that surrounds said shank portion, said coiled spring having an upper end engaging said top end wall, and a lower end that is opposite to said upper end, said thrust end having an enlarged end edge which, in cooperation with said shank portion, forms an abutment shoulder for engaging said lower end of said coiled spring, said tubular intermediate wall having outer and inner tubular wall surfaces opposite to each other in radial directions relative to the axis, said outer tubular wall surface having an access hole which extends radially through said inner tubular wall surface, said retaining member having a locking pin which is received in said access hole and which is radially movable between a locking position where said locking pin abuts said enlarged end edge against the biasing action, and a releasing position where said locking pin is retracted to release said enlarged end edge so that said coupling rod is forced by virtue of the biasing action to move to the retracted position, said triggering member being pivotally mounted on said outer tubular wall surface at a fulcrum point, and including a weight end formed integrally with said locking pin, and a power end disposed at an opposite side of said weight end relative to said fulcrum point so as to be actuated to move said locking pin to the releasing position.

11. The disposable syringe according to claim 1, wherein said grip member includes a second female screw thread segment which is disposed on said rear surrounding region, and a second male screw thread segment which is disposed on said surrounding gripped portion, said second male screw thread segment threadedly engaging said second female screw thread segment such that the resisting force is provided between said surrounding gripped portion and said rear surrounding region, and such that screw-out movement of said second male screw thread segment relative to said second female screw thread segment results in disappearance of the resisting force so as to permit disengagement of said surrounding gripped portion from said rear surrounding region, said central anchored area having an engaging recess which confronts said anchoring portion and which extends in the longitudinal direction so as to engage said anchoring portion, and a third female screw thread segment disposed in said engaging recess;

said anchoring portion having a third male screw thread segment, rotation of said third male and female screw thread segments relative to each other permitting engagement of said central anchored area with said anchoring portion, thereby providing the holding force.

12. The disposable syringe according to claim 1, further comprising a catheter hub which defines a duct therein, and which includes a sleeve portion that is sleeved on said barrel, and a tip portion opposite to said sleeve portion along the axis, and a tubular catheter which has a proximate segment that is disposed in said tip portion and that extends along the axis to communicate fluidly with said duct, and a distal segment that extends from said proximate segment along the axis to project outwardly of said tip portion, said needle cannula extending through said tubular catheter to terminate at a tip end that projects outwardly of said distal segment of said tubular catheter.

13. The disposable syringe according to claim 1, wherein said triggering member is an enlarged end edge which extends from said thrust end of said coupling rod, and which, in cooperation with said shank portion, forms an abutment shoulder for engaging said lower end of said coiled spring, said retaining member having a retaining groove which is formed in said inner tubular wall surface, and a protrusion which is formed on and which extends radially from said enlarged end edge so as to releasably engage said retaining groove.

14. The disposable syringe according to claim 1, wherein said accommodation chamber includes front and rear chamber regions which are respectively proximate to said top and bottom end walls, said rear chamber region being of a dimension larger than that of said front chamber region so as to clear the way for said biasing member when said biasing member biases said coupling rod towards the retracted position.

* * * * *